United States Patent
Pingleton et al.

(10) Patent No.: US 9,295,459 B2
(45) Date of Patent: Mar. 29, 2016

(54) SURGICAL ACCESS SYSTEM

(71) Applicant: Applied Medical Resources Corporation, Rancho Santa Margarita, CA (US)

(72) Inventors: Edward D. Pingleton, Rancho Santa Margarita, CA (US); Charles C. Hart, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 14/574,987

(22) Filed: Dec. 18, 2014

(65) Prior Publication Data

US 2015/0173736 A1    Jun. 25, 2015

Related U.S. Application Data

(63) Continuation of application No. 13/105,179, filed on May 11, 2011, now Pat. No. 8,932,214, which is a continuation of application No. 11/245,709, filed on Oct. 7, 2005, now Pat. No. 7,951,076, which is a (Continued)

(51) Int. Cl.
*A61B 17/02* (2006.01)
*A61B 17/34* (2006.01)
*A61B 17/00* (2006.01)

(52) U.S. Cl.
CPC ......... *A61B 17/0293* (2013.01); *A61B 17/3423* (2013.01); *A61B 17/3498* (2013.01); *A61B 2017/00265* (2013.01)

(58) Field of Classification Search
CPC ........... A61B 17/3417; A61B 17/3423; A61B 17/3431; A61B 2017/3419; A61B 2017/3429; A61B 2017/3425; A61B 2017/3427; A61M 39/00; A61M 2039/0054; A61M 2039/0063; A61M 2039/009
See application file for complete search history.

(56) References Cited

U.S. PATENT DOCUMENTS

| | | | |
|---|---|---|---|
| 558,364 | A | 4/1896 | Doolittle |
| 1,157,202 | A | 10/1915 | Bates et al. |

(Continued)

FOREIGN PATENT DOCUMENTS

| | | |
|---|---|---|
| DE | 26 05 148 A1 | 8/1977 |
| DE | 33 36 279 C2 | 1/1986 |

(Continued)

OTHER PUBLICATIONS

U.S. Appl. No. 10/902,756, filed Jul. 29, 2004; Title: Hand Access Port Device, now abandoned.

(Continued)

*Primary Examiner* — Anu Ramana
(74) *Attorney, Agent, or Firm* — Patrick Y. Ikehara

(57) ABSTRACT

The invention is directed to a surgical access system that provides access to a surgical area while maintaining pneumoperitoneum during laparoscopic surgery. The access system comprises a sheath retractor adapted to dilate a wound stretchable to a desired diameter and a detachable seal adapted to be removable from the sheath retractor. In another aspect, the detachable seal comprising a valve including a plurality of overlapping sheets defining an access channel that extends into communication with the incision in the patient. Each of the overlapping sheets includes a portion of the perimeter that is not fixed to the inner diameter of the ring, which provide open edges defining the access channel.

7 Claims, 22 Drawing Sheets

Related U.S. Application Data continuation of application No. 10/927,551, filed on Aug. 25, 2004, now abandoned, which is a continuation of application No. PCT/US2004/005484, filed on Feb. 25, 2004, and a continuation of application No. PCT/US2004/005487, filed on Feb. 25, 2004, and a continuation of application No. PCT/US2004/005361, filed on Feb. 24, 2004.

(60) Provisional application No. 60/449,857, filed on Feb. 25, 2003.

(56) References Cited

U.S. PATENT DOCUMENTS

| | | | |
|---|---|---|---|
| 1,598,284 | A | 8/1926 | Kinney |
| 1,690,995 | A | 11/1928 | Pratt |
| 1,180,466 | A | 6/1931 | Deutsch |
| 1,810,466 | A | 6/1931 | Deutsch |
| 2,219,564 | A | 10/1940 | Reyniers |
| 2,305,289 | A | 12/1942 | Coburg |
| 2,478,586 | A | 8/1949 | Krapp |
| 2,669,991 | A | 2/1954 | Curutchet |
| 2,695,608 | A | 11/1954 | Gibbon |
| 2,812,758 | A | 11/1957 | Blumenschein |
| 2,835,253 | A | 5/1958 | Borgeson |
| 2,853,075 | A | 9/1958 | Hoffman et al. |
| 3,039,468 | A | 6/1962 | Price |
| 3,057,350 | A | 10/1962 | Cowley |
| 3,111,943 | A | 11/1963 | Orndorff |
| 3,195,934 | A | 7/1965 | Parrish |
| 3,244,169 | A | 4/1966 | Baxter |
| 3,253,594 | A | 5/1966 | Matthews et al. |
| 3,313,299 | A | 4/1967 | Spademan |
| 3,329,390 | A | 7/1967 | Hulsey |
| 3,332,417 | A | 7/1967 | Blanford et al. |
| 3,347,226 | A | 10/1967 | Harrower |
| 3,347,227 | A | 10/1967 | Harrower |
| 3,397,692 | A | 8/1968 | Creager, Jr. et al. |
| 3,402,710 | A | 9/1968 | Paleschuck |
| 3,416,520 | A | 12/1968 | Creager, Jr. |
| 3,447,533 | A | 6/1969 | Spicer |
| 3,522,800 | A | 8/1970 | Lesser |
| 3,523,534 | A | 8/1970 | Nolan |
| 3,570,475 | A | 3/1971 | Weinstein |
| 3,656,485 | A | 4/1972 | Robertson |
| 3,685,786 | A | 8/1972 | Woodson |
| 3,717,151 | A | 2/1973 | Collett |
| 3,717,883 | A | 2/1973 | Mosher |
| 3,729,006 | A | 4/1973 | Wilder et al. |
| 3,729,027 | A | 4/1973 | Bare |
| 3,782,370 | A | 1/1974 | McDonald |
| 3,797,478 | A | 3/1974 | Walsh et al. |
| 3,799,166 | A | 3/1974 | Marsan |
| 3,807,393 | A | 4/1974 | McDonald |
| 3,828,764 | A | 8/1974 | Jones |
| 3,831,583 | A | 8/1974 | Edmunds et al. |
| 3,841,332 | A | 10/1974 | Treacle |
| 3,850,172 | A | 11/1974 | Cazalis |
| 3,853,126 | A | 12/1974 | Schulte |
| 3,853,127 | A | 12/1974 | Spademan |
| 3,856,021 | A | 12/1974 | McIntosh |
| 3,860,274 | A | 1/1975 | Ledstrom et al. |
| 3,861,416 | A | 1/1975 | Wichterle |
| 3,907,389 | A | 9/1975 | Cox et al. |
| 3,915,171 | A | 10/1975 | Shermeta |
| 3,965,890 | A | 6/1976 | Gauthier |
| 3,970,089 | A | 7/1976 | Saice |
| 3,996,623 | A | 12/1976 | Kaster |
| 4,000,739 | A | 1/1977 | Stevens |
| 4,016,884 | A | 4/1977 | Kwan-Gett |
| 4,024,872 | A | 5/1977 | Muldoon |
| 4,030,500 | A | 6/1977 | Ronnquist |
| 4,043,328 | A | 8/1977 | Cawood, Jr. et al. |
| 4,069,913 | A | 1/1978 | Harrigan |
| 4,083,370 | A | 4/1978 | Taylor |
| 4,096,853 | A | 6/1978 | Weigand |
| 4,112,932 | A | 9/1978 | Chiulli |
| 4,117,847 | A | 10/1978 | Clayton |
| 4,130,113 | A | 12/1978 | Graham |
| 4,177,814 | A | 12/1979 | Knepshield et al. |
| 4,183,357 | A | 1/1980 | Bentley et al. |
| 4,187,849 | A | 2/1980 | Stim |
| 4,188,945 | A | 2/1980 | Wenander |
| 4,217,664 | A | 8/1980 | Faso |
| 4,222,126 | A | 9/1980 | Boretos et al. |
| 4,228,792 | A | 10/1980 | Rhys-Davies |
| 4,239,036 | A | 12/1980 | Krieger |
| 4,240,411 | A | 12/1980 | Hosono |
| 4,253,201 | A | 3/1981 | Ross et al. |
| 4,254,973 | A | 3/1981 | Banjamin |
| 4,306,562 | A | 12/1981 | Osborne |
| 4,321,915 | A | 3/1982 | Leighton |
| 4,331,138 | A | 5/1982 | Jessen |
| 4,338,934 | A | 7/1982 | Spademan |
| 4,338,937 | A | 7/1982 | Lerman |
| 4,367,728 | A | 1/1983 | Mutke |
| 4,369,284 | A | 1/1983 | Chen |
| 4,399,816 | A | 8/1983 | Spangler |
| 4,402,683 | A | 9/1983 | Kopman |
| 4,411,659 | A | 10/1983 | Jensen et al. |
| 4,421,296 | A | 12/1983 | Stephens |
| 4,424,833 | A | 1/1984 | Spector et al. |
| 4,428,364 | A | 1/1984 | Bartolo |
| 4,430,081 | A | 2/1984 | Timmermans |
| 4,434,791 | A | 3/1984 | Darnell |
| 4,436,519 | A | 3/1984 | O'Neill |
| 4,454,873 | A | 6/1984 | Laufenberg et al. |
| 4,473,067 | A | 9/1984 | Schiff |
| 4,475,548 | A | 10/1984 | Muto |
| 4,485,490 | A | 12/1984 | Akers et al. |
| 4,488,877 | A | 12/1984 | Klein |
| 4,543,088 | A | 9/1985 | Bootman et al. |
| 4,550,713 | A | 11/1985 | Hyman |
| 4,553,537 | A | 11/1985 | Rosenberg |
| 4,555,242 | A | 11/1985 | Saudagar |
| 4,556,996 | A | 12/1985 | Wallace |
| 4,601,710 | A | 7/1986 | Moll |
| 4,610,665 | A | 9/1986 | Matsumoto et al. |
| 4,626,245 | A | 12/1986 | Weinstein |
| 4,634,424 | A | 1/1987 | O'Boyle |
| 4,634,432 | A | 1/1987 | Kocak |
| 4,644,951 | A | 2/1987 | Bays |
| 4,649,904 | A | 3/1987 | Krauter |
| 4,653,476 | A | 3/1987 | Bonnet |
| 4,654,030 | A | 3/1987 | Moll et al. |
| 4,655,752 | A | 4/1987 | Honkanen et al. |
| 4,673,393 | A | 6/1987 | Suzuki et al. |
| 4,673,394 | A | 6/1987 | Fenton |
| 4,691,942 | A | 9/1987 | Ford |
| 4,714,749 | A | 12/1987 | Hughes et al. |
| 4,738,666 | A | 4/1988 | Fuqua |
| 4,755,170 | A | 7/1988 | Golden |
| 4,760,933 | A | 8/1988 | Christner et al. |
| 4,776,843 | A | 10/1988 | Martinez et al. |
| 4,777,943 | A | 10/1988 | Chvapil |
| 4,784,646 | A | 11/1988 | Feingold |
| 4,796,629 | A | 1/1989 | Grayzel |
| 4,798,594 | A | 1/1989 | Hillstead |
| 4,802,694 | A | 2/1989 | Vargo |
| 4,808,168 | A | 2/1989 | Warring |
| 4,809,679 | A | 3/1989 | Shimonaka et al. |
| 4,828,554 | A | 5/1989 | Griffin |
| 4,842,931 | A | 6/1989 | Zook |
| 4,848,575 | A | 7/1989 | Nakamura et al. |
| 4,856,502 | A | 8/1989 | Ersfeld et al. |
| 4,863,430 | A | 9/1989 | Klyce et al. |
| 4,863,438 | A | 9/1989 | Gauderer et al. |
| 4,889,107 | A | 12/1989 | Kaufman |
| 4,895,565 | A | 1/1990 | Hillstead |
| 4,897,081 | A | 1/1990 | Poirier |
| 4,903,710 | A | 2/1990 | Jessamine et al. |
| 4,911,974 | A | 3/1990 | Shimizu et al. |
| 4,915,132 | A | 4/1990 | Hodge et al. |

(56) References Cited

U.S. PATENT DOCUMENTS

| | | |
|---|---|---|
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Rirchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,879 A * | 7/1993 | Ensminger et al. ...... 604/288.03 |
| 5,226,890 A | 7/1993 | Ianniruberto et al. |
| 5,234,455 A | 8/1993 | Mulhollan |
| 5,241,968 A | 9/1993 | Slater |
| 5,242,400 A | 9/1993 | Blake, III et al. |
| 5,242,409 A | 9/1993 | Buelna |
| 5,242,412 A | 9/1993 | Blake, III et al. |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| 5,279,575 A | 1/1994 | Sugarbaker |
| 5,290,310 A | 3/1994 | Makower et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Durdal et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |
| 5,514,133 A | 5/1996 | Golub et al. |
| 5,514,153 A | 5/1996 | Bonutti |
| 5,518,278 A | 5/1996 | Sampson |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |

(56) References Cited

U.S. PATENT DOCUMENTS

| | | |
|---|---|---|
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |
| 5,657,963 A | 8/1997 | Hinchliffe et al. |
| 5,658,272 A | 8/1997 | Hasson |
| 5,658,306 A | 8/1997 | Kieturakis |
| 5,662,615 A | 9/1997 | Blake, III |
| 5,672,168 A | 9/1997 | de la Torre et al. |
| 5,681,341 A | 10/1997 | Lunsford et al. |
| 5,683,378 A | 11/1997 | Christy |
| 5,685,854 A | 11/1997 | Green et al. |
| 5,685,857 A | 11/1997 | Negus et al. |
| 5,697,914 A | 12/1997 | Brimhall |
| 5,707,703 A | 1/1998 | Rothrum et al. |
| 5,709,664 A | 1/1998 | Vandenbroek et al. |
| 5,713,858 A | 2/1998 | Heruth et al. |
| 5,713,869 A | 2/1998 | Morejon |
| 5,720,730 A | 2/1998 | Blake, III |
| 5,725,536 A | 3/1998 | Oberlin et al. |
| 5,728,103 A | 3/1998 | Picha et al. |
| 5,730,748 A | 3/1998 | Fogarty et al. |
| 5,735,791 A | 4/1998 | Alexander et al. |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,760,117 A | 6/1998 | Chen |
| 5,769,783 A | 6/1998 | Fowler |
| 5,782,812 A | 7/1998 | Hart et al. |
| 5,782,817 A | 7/1998 | Franzel et al. |
| 5,782,859 A | 7/1998 | Nicholas et al. |
| 5,788,676 A | 8/1998 | Yoon |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,803,923 A | 9/1998 | Singh-Derewa et al. |
| 5,807,350 A | 9/1998 | Diaz |
| 5,810,712 A | 9/1998 | Dunn |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom et al. |
| 5,819,375 A | 10/1998 | Kastner |
| 5,820,555 A | 10/1998 | Watkins, III et al. |
| 5,820,600 A | 10/1998 | Carlson et al. |
| 5,830,191 A | 11/1998 | Hildwein et al. |
| 5,832,925 A | 11/1998 | Rothrum |
| 5,836,871 A | 11/1998 | Wallace et al. |
| 5,841,298 A | 11/1998 | Huang |
| 5,842,971 A | 12/1998 | Yoon |
| 5,848,992 A | 12/1998 | Hart et al. |
| 5,853,395 A | 12/1998 | Crook et al. |
| 5,853,417 A | 12/1998 | Fogarty et al. |
| 5,857,461 A | 1/1999 | Levitsky et al. |
| 5,860,995 A | 1/1999 | Berkelaar |
| 5,865,728 A | 2/1999 | Moll et al. |
| 5,865,729 A | 2/1999 | Meehan et al. |
| 5,865,807 A | 2/1999 | Blake, III |
| 5,865,817 A | 2/1999 | Moenning et al. |
| 5,871,474 A | 2/1999 | Hermann et al. |
| 5,876,413 A | 3/1999 | Fogarty et al. |
| 5,879,368 A | 3/1999 | Hoskin et al. |
| 5,882,344 A | 3/1999 | Stouder, Jr. |
| 5,884,639 A | 3/1999 | Chen |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,913,847 A | 6/1999 | Yoon |
| 5,916,198 A | 6/1999 | Dillow |
| 5,916,232 A | 6/1999 | Hart |
| 5,919,476 A | 7/1999 | Fischer et al. |
| 5,931,832 A | 8/1999 | Jensen |
| 5,947,922 A | 9/1999 | MacLeod |
| 5,951,467 A | 9/1999 | Picha et al. |
| 5,951,588 A | 9/1999 | Moenning |
| 5,957,888 A | 9/1999 | Hinchiffe et al. |
| 5,957,913 A | 9/1999 | de la Torre et al. |
| 5,962,572 A | 10/1999 | Chen |
| 5,964,781 A | 10/1999 | Mollenauer et al. |
| 5,976,174 A | 11/1999 | Ruiz |
| 5,989,232 A | 11/1999 | Yoon |
| 5,989,233 A | 11/1999 | Yoon |
| 5,989,266 A | 11/1999 | Foster |
| 5,993,471 A | 11/1999 | Riza et al. |
| 5,993,485 A | 11/1999 | Beckers |
| 5,994,450 A | 11/1999 | Pearce |
| 5,997,515 A | 12/1999 | de la Torre et al. |
| 6,004,303 A | 12/1999 | Peterson |
| 6,010,494 A | 1/2000 | Schafer et al. |
| 6,017,355 A | 1/2000 | Hessel et al. |
| 6,018,094 A | 1/2000 | Fox |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,042,573 A | 3/2000 | Lucey |
| 6,045,535 A | 4/2000 | Nun |
| 6,048,309 A | 4/2000 | Flom et al. |
| 6,050,871 A | 4/2000 | Chen |
| 6,053,934 A | 4/2000 | Andrews et al. |
| 6,059,816 A | 5/2000 | Moenning |
| 6,066,117 A | 5/2000 | Fox et al. |
| 6,068,639 A | 5/2000 | Fogarty et al. |
| 6,076,560 A | 6/2000 | Stahle et al. |
| 6,077,288 A | 6/2000 | Shimomura |
| 6,086,603 A | 7/2000 | Termin et al. |
| 6,090,043 A | 7/2000 | Austin et al. |
| 6,099,506 A | 8/2000 | Macoviak et al. |
| 6,110,154 A | 8/2000 | Shimomura et al. |
| 6,123,689 A | 9/2000 | To et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |

(56) References Cited

U.S. PATENT DOCUMENTS

| | | |
|---|---|---|
| 6,164,279 A | 12/2000 | Tweedle |
| 6,171,282 B1 | 1/2001 | Ragsdale |
| 6,183,486 B1 | 2/2001 | Snow et al. |
| 6,197,002 B1 | 3/2001 | Peterson |
| 6,217,555 B1 | 4/2001 | Hart et al. |
| 6,217,590 B1 | 4/2001 | Levinson |
| 6,224,612 B1 | 5/2001 | Bates et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,533 B1 | 7/2001 | Fadem et al. |
| 6,254,534 B1 | 7/2001 | Butler et al. |
| 6,258,065 B1 | 7/2001 | Dennis et al. |
| 6,264,604 B1 | 7/2001 | Kieturakis et al. |
| 6,267,751 B1 | 7/2001 | Mangosong |
| 6,276,661 B1 | 8/2001 | Laird |
| 6,287,280 B1 | 9/2001 | Lampropoulos et al. |
| 6,315,770 B1 | 11/2001 | de la Torre et al. |
| 6,319,246 B1 | 11/2001 | de la Torre et al. |
| 6,322,541 B2 | 11/2001 | West |
| 6,325,384 B1 | 12/2001 | Berry, Sr. et al. |
| 6,346,074 B1 | 2/2002 | Roth |
| 6,371,968 B1 | 4/2002 | Kogasaka et al. |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B2 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Lui et al. |
| 7,105,009 B2 | 9/2006 | Johnson |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |

(56) References Cited

U.S. PATENT DOCUMENTS

| | | |
|---|---|---|
| 7,344,546 B2 | 3/2008 | Wulfman et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,841,765 B2 | 11/2010 | Keller |
| 7,850,667 B2 | 12/2010 | Gresham |
| 7,867,164 B2 | 1/2011 | Butler et al. |
| 7,878,974 B2 | 2/2011 | Brustad et al. |
| 7,883,461 B2 | 2/2011 | Albrecht et al. |
| 7,892,172 B2 | 2/2011 | Albrecht et al. |
| 7,896,889 B2 | 3/2011 | Mazzocchi et al. |
| 7,909,760 B2 | 3/2011 | Albrecht et al. |
| 7,913,697 B2 | 3/2011 | Nguyen et al. |
| 7,930,782 B2 | 4/2011 | Chen |
| 7,998,068 B2 | 8/2011 | Bonadio et al. |
| 8,021,296 B2 | 9/2011 | Bonadio |
| 8,317,690 B2 | 11/2012 | Ransden |
| RE44,380 E | 7/2013 | de la Torre et al. |
| 8,574,153 B2 | 11/2013 | Richard |
| RE44,790 E | 3/2014 | de la Torre et al. |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0004253 A1 | 1/2003 | Chen |
| 2003/0014076 A1 | 1/2003 | Mollenauer et al. |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor et al. |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlbert et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0080319 A1 | 4/2005 | Dinkler, II et al. |
| 2005/0090713 A1 | 4/2005 | Gonzales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 | 4/2007 | Albrecht et al. |
| 2007/0088204 A1 | 4/2007 | Albrecht |

(56) References Cited

U.S. PATENT DOCUMENTS

| | | | |
|---|---|---|---|
| 2007/0093695 A1 | 4/2007 | Bonadio et al. |
| 2007/0118175 A1 | 5/2007 | Butler et al. |
| 2007/0149859 A1 | 6/2007 | Albrecht |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0270752 A1 | 11/2007 | Labombard |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0182282 A1 | 7/2009 | Okihisa |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegal et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |
| 2010/0261975 A1 | 10/2010 | Huey et al. |
| 2010/0286484 A1 | 11/2010 | Stellon et al. |
| 2010/0298646 A1 | 11/2010 | Stellon et al. |
| 2011/0021877 A1 | 1/2011 | Fortier et al. |
| 2011/0028891 A1 | 2/2011 | Okoniewski |
| 2011/0034935 A1 | 2/2011 | Kleyman |
| 2011/0034946 A1 | 2/2011 | Kleyman |
| 2011/0034947 A1 | 2/2011 | Kleyman |
| 2011/0071462 A1 | 3/2011 | Ewers et al. |
| 2011/0071463 A1 | 3/2011 | Ewers et al. |
| 2012/0095297 A1 | 4/2012 | Dang et al. |

FOREIGN PATENT DOCUMENTS

| | | |
|---|---|---|
| DE | 37 39 532 | 12/1988 |
| DE | 37 37 121 | 5/1989 |
| DE | 296 00 939 | 6/1996 |
| DE | 19828099 | 12/1999 |
| EP | 0 113 520 | 7/1984 |
| EP | 0 142 262 | 5/1985 |
| EP | 0 517 248 | 12/1992 |
| EP | 0 537 768 | 4/1993 |
| EP | 0 807 416 | 11/1997 |
| EP | 0 849 517 | 6/1998 |
| EP | 0950376 | 10/1999 |
| EP | 1 118 657 | 7/2001 |
| EP | 1 125 552 | 8/2001 |
| EP | 1 312 318 | 5/2003 |
| EP | 1 407 715 | 4/2004 |
| EP | 2 044 889 | 4/2009 |
| EP | 2 272 450 A2 | 1/2011 |
| EP | 2 340 792 | 7/2011 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| RU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |

(56) References Cited

FOREIGN PATENT DOCUMENTS

| | | |
|---|---|---|
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/26559 | 4/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO 03/034908 | 5/2003 |
| WO | WO 03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2007/044849 | 4/2007 |
| WO | WO 2008/015566 | 2/2008 |
| WO | WO 2008/093313 | 8/2008 |
| WO | WO 2008/121294 | 10/2008 |
| WO | WO 2010/045253 | 4/2010 |
| WO | WO 2010/082722 | 7/2010 |
| WO | WO 2010/104259 | 9/2010 |

OTHER PUBLICATIONS

U.S. Appl. No. 10/802,125, filed Mar. 15, 2004; Title: Surgical Guide Valve, now abandoned.
U.S. Appl. No. 10/927,551, filed Aug. 25, 2004; Title: Surgical Access System, now abandoned.
U.S. Appl. No. 10/695,295, filed Oct. 28, 2003; Title: Surgical Gel Seal.
U.S. Appl. No. 11/132,741, filed May 18, 2005; Title: Gas-Tight Seal Accomodating Surgical Instruments With a Wide Range of Diameters.
U.S. Appl. No. 11/245,709, filed Oct. 7, 2005; Title: Surgical Access System.
U.S. Appl. No. 11/330,661, filed Jan. 12, 2006; Title: Sealed Surgical Access Device.
U.S. Appl. No. 11/564,409, filed Nov. 29, 2006; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011; Title: Hand Access Laparoscopic Device.
U.S. Appl. No. 13/008,728, filed Jan. 18, 2011; Title: Wound Retractor With Gel Cap.
U.S. Appl. No. 13/023,334, filed Feb. 8, 2011; Title: Circular Surgical Retractor.
U.S. Appl. No. 13/031,892, filed Feb. 22, 2011; Title: Wound Retractor.
U.S. Appl. No. 13/050,042, filed Mar. 17, 2011; Title: Split Hoop Wound Retractor With Gel Pad.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc., dated 1999.
European Patent Office, European Search Report for European Application No. EP 10 18 4681, entitled "Wound Retraction Apparatus and Method",dated Nov. 22, 2010.
European Patent Office, European Search Report for European Application No. EP 10 18 4608, entitled "Wound Retraction Apparatus and Method", dated Nov. 22, 2010.
European Patent Office, European Search Report for European Application No. EP 10 18 4648, entitled "Wound Retraction Apparatus and Method", dated Nov. 22, 2010.
European Patent Office, European Search Report for European Application No. EP 10 18 4731, entitled "Wound Retraction Apparatus and Method", dated Nov. 22, 2010.
European Patent Office, European Search Report for European Application No. EP 10 18 4661, entitled "Wound Retraction Apparatus and Method", dated Nov. 22, 2010.
European Patent Office, European Search Report for European Application No. EP 10 18 4677, entitled "Wound Retraction Apparatus and Method", dated Nov. 22, 2010.
European Patent Office, European Search Report for European Application No. EP 10 18 9325, entitled "Split Hoop Wound Retractor", dated Dec. 14, 2010.
European Patent Office, European Search Report for European Application No. EP 10 18 9327, entitled "Split Hoop Wound Retractor", dated Dec. 14, 2010.

(56) References Cited

OTHER PUBLICATIONS

European Patent Office, European Search Report for European Application No. EP 10 18 9328, entitled "Split Hoop Wound Retractor", dated Dec. 15, 2010.
European Patent Office, European Search Report for European Application No. EP 04 00 2888, entitled "Hand Access Port Device", dated Sep. 10, 2004.
European Patent Office, European Search Report for European Application No. EP 04 00 2889, entitled "Hand Access Port Device", dated Sep. 13, 2004.
European Patent Office, International Search Report and the Written Opinion of the International Searching Authority for International Application No. PCT/US2006/040154, mailed Jan. 30, 2007.
European Patent Office, International Search Report and the Written Opinion of the International Searching Authority for International Application No. PCT/US2006/040073, mailed Jan. 26, 2007.
European Patent Office, International Search Report and the Written Opinion of the International Searching Authority for International Application No. PCT/US2006/039905, mailed Jan. 17, 2007.
European Patent Office, International Search Report and the Written Opinion of the International Searching Authority for International Application No. PCT/US2006/039883, mailed Jan. 31, 2007.
European Patent Office, International Search Report and the Written Opinion of the International Searching Authority for International Application No. PCT/US2006/039800, mailed Apr. 16, 2007.
European Patent Office, International Search Report and the Written Opinion of the International Searching Authority for International Application No. PCT/US2006/039799, mailed Mar. 27, 2007.
European Patent Office, European Search Report for European Application No. EP 08253236 dated Feb. 10, 2009.
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484, mailed on Nov. 12, 2004.
International Searching Authority/US, International Search Report and the Written Opinion of the International Searching Authority for International Application No. PCT/US01/29682, mailed on Jun. 14, 2002.
McSweeney, Cannulation of the Rumen in Cattle and Buffaloes, Australian Veterinary Journal, Aug. 1989, vol. 66, No. 8, pp. 266-268.
Neil Sheehan, Supplemental Expert Report of Neil Sheehan, Re: U.S. Pat. No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan, dated 1992.
The International Bureau of WIPO, International Preliminary Report on Patentability for International Application No. PCT/US2004/028250, dated Aug. 29, 2006.
The International Bureau of WIPO, International Preliminary Report on Patentability for International Application No. PCT/US2006/039799, dated Apr. 16, 2008.
The International Bureau of WIPO, International Preliminary Report on Patentability for International Application No. PCT/US2006/039800 dated Apr. 16, 2008.
Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.
Kagaya, "Laparascopic cholecystecomy via two ports, using the Twin-Port" system, J. Hepatobiliary Pancreat Surg (2001) 8:76-80, dated Feb. 20, 2001.
Declaration of John R. Brustad dated Dec. 10, 2009, submitted in U.S. Appl. No. 11/548,955, including Appendices A-D regarding product sales brochures and production drawings from 2001 and 2005.
International Search Report and Written Opinion for PCT/IE2005/000113, mailed on Feb. 22, 2006.
International Searching Authority-US, International Search Report and Written Opinion of the International Searching Authority for International Application No. PCT/US04/25511, mailed Nov. 7, 2007.
International Bureau of WIPO, International Report on Patentability for International Application No. PCT/US04/25511, mailed Dec. 6, 2007.
International Search Report and Written Opinion for PCT/IE2007/000050 mailed on Aug. 13, 2007.
The International Searching Authority, The International Search Report and Written Opinion of the International Searching Authority for International Application No. PCT/US08/63445, mailed Sep. 29, 2008.
The International Searching Authority, The International Search Report and Written Opinion of the International Searching Authority for International Application No. PCT/US08/063463 mailed Sep. 10, 2008.
The International Bureau of WIPO, International Preliminary Report on Patentability for International Application No. PCT/US2008/063463, entitled "Surgical Retractor", dated Nov. 17, 2009.
The International Bureau of WIPO, International Preliminary Report on Patentability for International Application No. PCT/US08/63445, entitled "Surgical Retractor with Gel Pad", dated Nov. 17, 2009.
International Searching Authority—European Patent Office, The International Search Report and Written Opinion for International Application No. PCT/US2011/054266, mailed Feb. 9, 2012.
European Patent Office, European Search Report for European Patent No. 11172709.5, dated Aug. 16, 2011.
European Patent Office, European Search Report for European Patent No. 11172706.1, dated Aug. 16, 2011.
European Patent Office, European Search Report for European Patent No. 12151288, dated Feb. 10, 2012.
European Patent Office, European Search Report for European Patent No. 08755332, dated Apr. 18, 2012.
European Patent Office, Supplementary European Search Report for European Patent Application No. 08755322, dated Apr. 18, 2012.
European Patent Office, Supplementary European Search Report for European Patent Application No. 08755336, dated Jun. 15, 2012.
Harold W. Harrower, M.D., Isolation of Incisions into Body Cavities, The American Journal of Surgery, vol. 116, pp. 824-826, Dec. 1968.
International Searching Authority—European Patent Office, The International Search Report and Written Opinion for International Application No. PCT/US2013/037213, mailed Jul. 3, 2013.

* cited by examiner

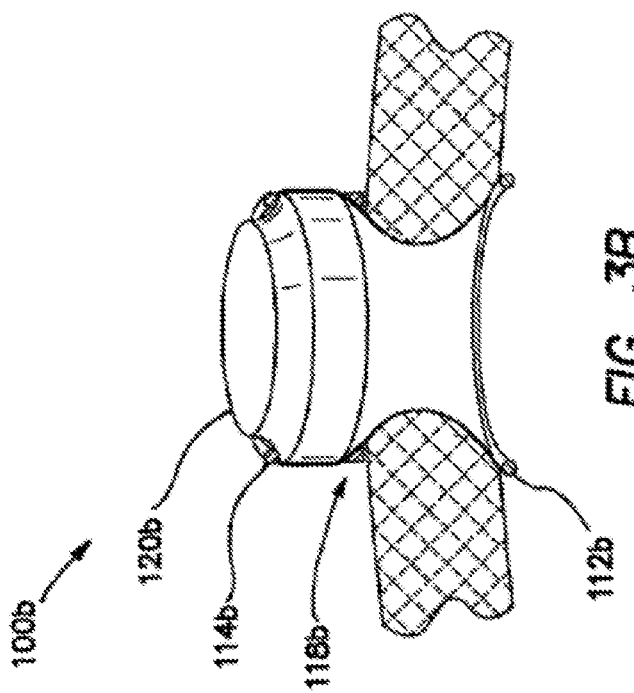
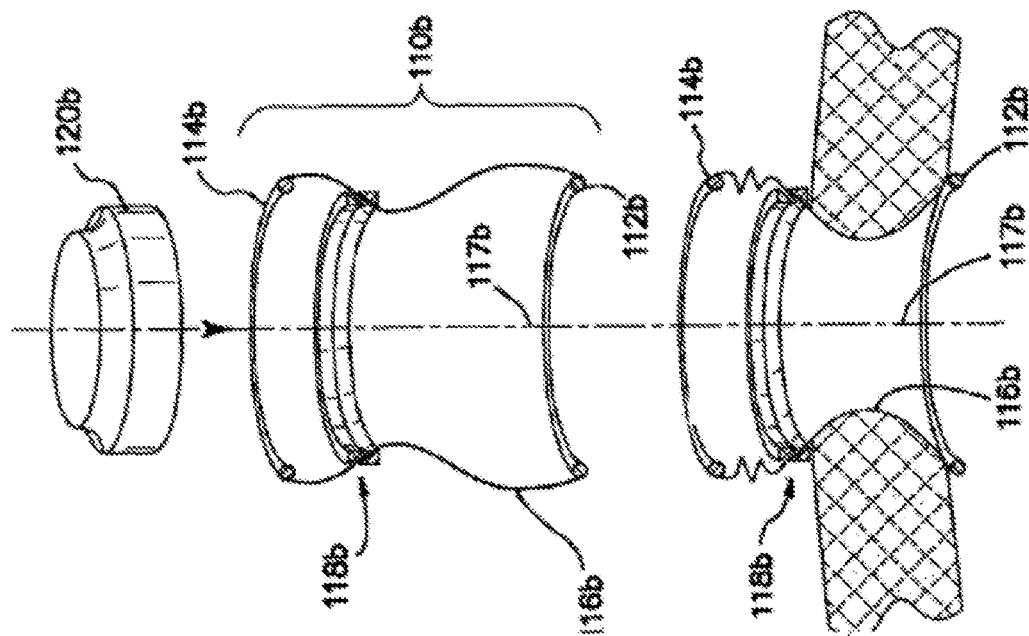
FIG. 3B
FIG. 3A

SURGICAL ACCESS SYSTEM

CROSS-REFERENCE TO RELATED APPLICATIONS

This is a continuation of U.S. patent application Ser. No. 13/105,179, filed May 11, 2011, which is a continuation of U.S. patent application Ser. No. 11/245,709, filed Oct. 7, 2005, now U.S. Pat. No. 7,951,076, which is a continuation of U.S. patent application Ser. No. 10/927,551, filed Aug. 25, 2004, which is a continuation of (1) PCT application Serial No. PCT/US2004/005484, entitled "Sealed Surgical Access Device," filed on Feb. 25, 2004, (2) PCT application Serial No. PCT/US2004/005487, entitled "Wound Retractor for Use in Hand-Assisted Laparoscopic Surgery," filed on Feb. 25, 2004, and (3) PCT application Serial No. PCT/US2004/005361, entitled "Apparatus and Method for Illuminating a Peritoneal Cavity During Laparoscopic Surgery," filed on Feb. 24, 2004, all of which claim priority to (4) provisional application Ser. No. 60/449,857, filed on Feb. 25, 2003, entitled "Hand-Assisted Laparoscopy Apparatus and Method," all of which are fully incorporated herein by reference in their entireties.

BACKGROUND

This invention generally relates to surgical access systems that facilitate sealed access across a body wall and into a body cavity during a laparoscopic surgical procedure.

During laparoscopic surgery, it is desirable to inflate the abdominal cavity in order to increase the volume of the working space. This is accomplished with an insufflation gas which must be maintained at a pressure sufficient to inflate the abdomen. Maintaining the pressure of the insufflation gas is difficult when it is also desirable to insert instrumentation through the abdominal wall. If a surgeon is interested in inserting his or her hand in a hand-assisted laparoscopic procedure, the maintenance of insufflation pressure is even more difficult. Currently, several devices exist that accomplish this surgical need although they suffer from drawbacks such as difficult placement and cumbersome use. For example, these hand-assisted devices require elaborate mechanisms such as inflatable cuffs and adhesives to seal around a surgeon's wrist or forearm to maintain the insufflation gases. As such, there is a need for a special seal formed around the wrist or forearm of a surgeon to prevent the escape of insufflation gases. Moreover, it is desirable that the wound be retracted, protected and fixed while maintaining the insufflation seal.

SUMMARY

The invention is directed to a hand access system that provides hand access to a surgical area while maintaining pneumoperitoneum during laparoscopic surgery. The hand access system comprises a sheath retractor adapted to dilate a wound stretchable to a desired diameter, the sheath retractor includes a first ring being adapted for disposition interiorly of the wound, a second ring being adapted for disposition exteriorly of the wound, and a sheath being disposed in a generally cylindrical form between the first ring and the second ring and operable to exert a radial retraction force on the wound. The hand access system further comprises a detachable hand seal adapted to be attached and detached from the second ring of the sheath retractor. In particular, the hand seal can be detached from the sheath retractor to convert the hand access system from laparoscopic surgery to open surgery. In one aspect, the first ring, second ring and sheath are formed from an elastomeric material, and the hand seal is formed of a gel material and includes a slit providing an instrument seal in the presence of an instrument or hand and a zero seal in the absence of the instrument or hand. The gel material includes, for example, a thermoplastic base such as Kraton® and an oil. The resulting elastomer has excellent tear strength, elongation greater than 1,000 percent, a very low durometer or hardness, and biocompatibility. It is appreciated that the first ring has a first diameter and the second ring has a second diameter, and the first and second diameters are greater than the desired diameter of the wound.

In another aspect, the sheath retractor further comprises a third ring disposed circumferentially of the sheath and moveable between a plurality of positions between the first ring and the second ring, each of the positions being associated with a different retraction force, the third ring being adapted for disposition exteriorly of the wound. The sheath retractor may further comprise means for retaining the third ring at one of the plurality of positions in order to provide the desired radial retraction force associated with that position. The retaining means may comprise a fourth ring adapted to interlock with the third ring to fix the sheath at the desired position. The retaining means may include a wedge disposed between the third ring and the fourth ring.

In yet another aspect of the invention, the hand access system may further comprise an adapter having a first adapter cavity for releasably attaching to a ring of the retractor sheath and a second adapter cavity for releasably attaching to the hand seal. The first adapter cavity has a first diameter and the second adapter cavity has a second diameter.

In other aspects of the invention, the hand seal may include a cavity to receive the second ring of the sheath retractor, the hand seal may further comprise a latch on an inner diameter for latching the third ring, and the third ring may comprise at least a hook to latch the hand seal as the hand seal is attached to the sheath retractor. To facilitate sealing of the peritoneum, a conformable gasket may be provided that may be attached to the first ring or to the sheath of the sheath retractor, or the conformable gasket may float unattached to the sheath and interiorly of the wound.

In another aspect of the invention, the hand access system may comprise a detachable iris seal in place of the hand seal that is adapted to be attached and detached from the sheath retractor. The iris seal comprises a first iris ring, a second iris ring coaxially attached to the first iris ring, and a cylindrical elastic member connected to the first and second iris rings and having an opening. With this aspect, the first and second iris rings operate to rotate relative to one another in either direction to open or close the opening of the cylindrical elastic member. More specifically, the first and second iris rings may be rotated in opposite directions to create an airtight constriction in the middle of the elastic member. After rotation, at least one of the first and second iris rings may be de-rotated to loosen or enlarge the constriction of the elastic member.

Each of the iris rings may comprise a plurality of tracks to allow the iris rings to be relatively rotated at predetermined angles. In yet another aspect, the iris seal may further comprise a spring connecting the first and second iris rings to further facilitate a complete opening, a partial constriction or an airtight constriction of the opening of the elastic member. The spring operates to automatically pull and rotate the iris rings after de-rotation. In particular, as an object is withdrawn from the iris seal, the spring contracts and causes the sheath constriction to tighten automatically. The spring may be formed from an elastomeric material. It is appreciated that the amount the spring stretches and contracts is determined by the length of the spring. Each of the iris springs may comprise a hollow frame and a plurality of interlocking tracks. The interlocking tracks operate to encase the spring to prevent the spring from crossing into an instrument or hand passage area within the iris rings. The interlocking tracks also operate to open and close the seal at predetermined angles.

In another aspect of the invention, there is disclosed a surgical access device adapted for disposition relative to an incision in a patient comprising a valve including a plurality of overlapping sheets defining an access channel, and a ring having an inner diameter for holding the valve by fixing each of the overlapping sheets along a portion of the perimeter, the access channel extends into communication with the incision in the patient. With this aspect, each of the overlapping sheets includes a portion of the perimeter that is not fixed to the inner diameter of the ring. It is appreciated that the non-fixed portions provide open edges defining the access channel. In one aspect, the open edges slightly overlap for about 0.25" at the center of the ring. The hand access device may further comprise a septum seal formed at the proximal end and at the distal end of the ring, the septum seal having a hole formed at the center of the seal. It is further appreciated that the open edges of the non-fixed portions may have different shapes including at least one of a straight edge, concave, convex and a cross-configuration.

In yet another aspect of the invention, there is disclosed a surgical access device adapted for disposition relative to an incision in a patient comprising a plurality of septum layers each having a hole at the center of the septum layer and a first diameter, a ball sandwiched between the septum layers and having a second diameter greater than the first diameter, and a ring having an inner diameter for affixing the plurality of septum layers along the perimeter. In another aspect, a surgical access device facilitating a sealing relationship with an instrument or an arm of a surgeon extending through the device and into an incision in a patient is disclosed, the access device comprising a valve structure including a plurality of overlapping sheets defining an access channel, the valve in a first state forming a zero seal in the absence of the instrument or the arm of the surgeon extending through the valve structure, the valve in a second state forming an instrument seal in the presence of the instrument or the arm of the surgeon extending through the valve structure, and the access channel extends into communication with the incision in the patient.

These and other features of the invention will become more apparent with a discussion of the various embodiments in reference to the associated drawings.

BRIEF DESCRIPTION OF THE DRAWINGS

The accompanying drawings, which are included in and constitute a part of this specification, illustrate the embodiments of the invention and, together with the description, explain the features and principles of the invention. In the drawings:

FIGS. 3A-3E illustrate axial perspective views and cross-sectional views of a hand access system in accordance with another embodiment of the invention including a one-way mechanism;

DETAILED DESCRIPTION

Figure 1:
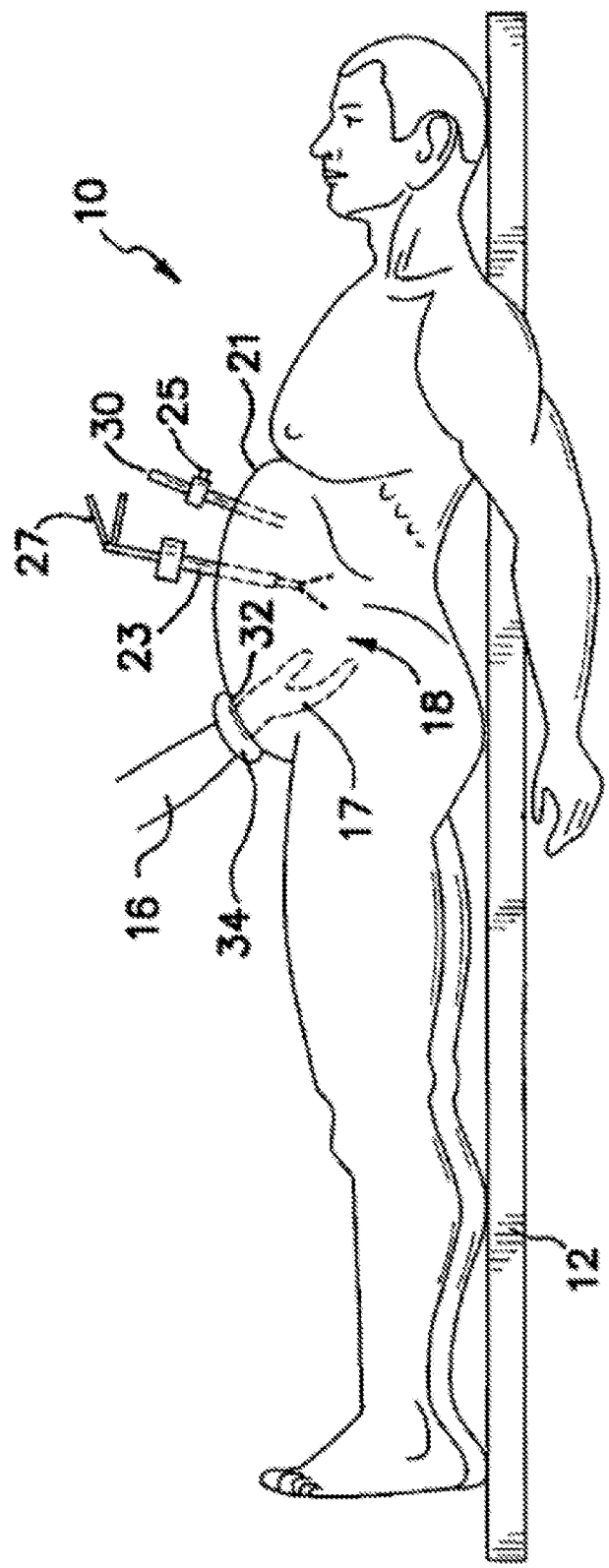
FIG. 1 is a perspective view showing a patient prone on an operating table with his abdomen insufflated and with instrument access provided by trocar and the access device of the present invention.

Referring to FIG. 1, there is shown a typical abdominal surgery on a patient 10 in a prone position on an operating table 12. FIG. 1 further illustrates a surgeon having an arm 16 and a hand 17 performing the surgery. In the illustrated example, the operative procedure is performed within an abdominal cavity 18 with instrument access provided through an abdominal wall 21. In this type of operation, commonly referred to as laparoscopic surgery, trocars 23 and 25 are commonly used to provide minimally invasive access through the abdominal wall 21 for instruments such as a grasper 27 and an endoscope 30. In addition, it is desirable that the surgeon be able to insert his/her hand 17 through the abdominal wall 21 and into the abdominal cavity 18. The insertion of the hand 17 provides the surgeon with direct access to various elements of the anatomy.

In order to accommodate the hand 17 and arm 16 of the surgeon, a small incision 32 is typically created in the abdominal wall 21. An access device 34 of the present invention can be provided to further facilitate this access by the hand 17 of the surgeon. Particularly in the case of laparoscopic surgery, it is advantageous to insufflate the abdominal cavity 18 with a gas, such as carbon dioxide, in order to elevate the abdominal wall 21 and thereby increase the volume of the working space within the cavity 18. Maintenance of this insufflation pressure, commonly referred to as pneumoperitoneum, is particularly difficult where access is desired across the abdominal wall 21, for example, through the trocars 23, 25, as well as the access device 34. For this reason, a substantial effort has been directed to providing such access devices with sealing characteristics both in the presence of instruments and in the absence of instruments, such as the grasper 27, scope 30 and hand 17.

Were it not for the desire to maintain the pneumoperitoneum, there would be no need for the trocars 23, 25 or the access device 34. That is, one would merely cut an incision in the abdominal wall 21 and insert the instrument directly through the incision. However, without appropriate valves or seals, the insufflation gases would merely escape through the incision 32. This would be particularly detrimental in the case of the incision 32 which must be sufficiently large to accept the hand 17 of the surgeon. Thus, the access device 34 operates to form with the incision 32 to provide an access or working channel, and to provide a valve or other sealing structure across the working channel in order to maintain the pneumoperitoneum.

Figure 2A:
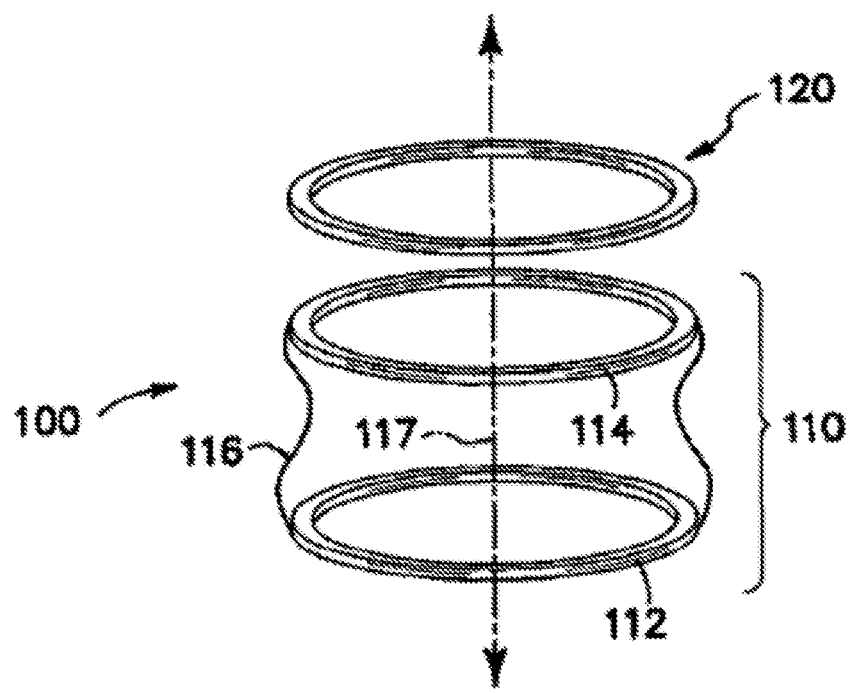
FIGS. 2A and 2B illustrate a perspective view and a cross-sectional view, respectively, of a hand access system in accordance with a first embodiment of the invention.
Figure 2B:
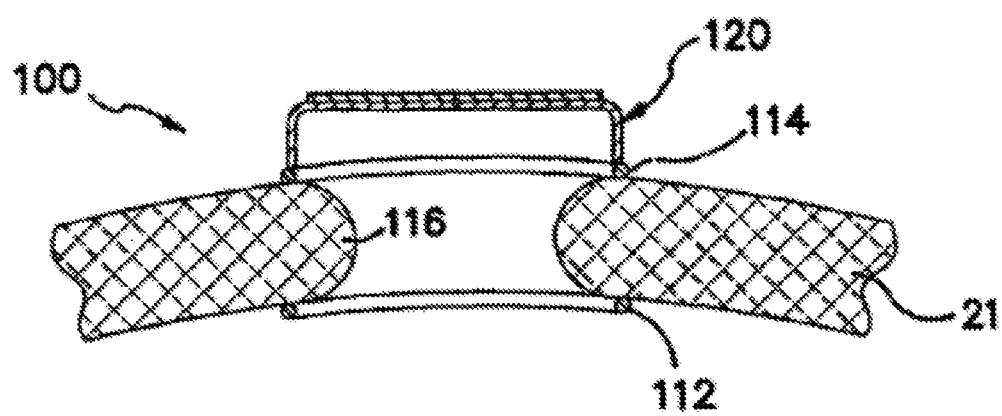

Referring to FIGS. 2A and 2B, there are shown a perspective view and a cross-sectional view, respectively, of a hand access system 100 of the invention. The hand access system 100 provides hand access to a surgical area such as the abdominal cavity 18 while maintaining pneumoperitoneum during laparoscopic surgery. The hand access system 100 comprises a sheath retractor 110 including a peritoneal ring 112, a proximal ring 114, and a sheath 116 extending along an axis 117 connecting the peritoneal ring 112 and the proximal ring 114. The sheath 116 has a generally cylindrical configuration that may be retracted to protect an incision within a body cavity such as the abdominal wall 21. The peritoneal ring 112 and proximal ring 114 are disposed in respective planes which extend radially of the axis 117. The hand access system 100 further comprises a detachable hand seal 120 that is operably attachable and detachable to the proximal ring 114 of the sheath retractor 110 as illustrated in FIG. 2B to permit insufflation. It is appreciated that the hand seal 120 can be separated from the sheath retractor 110 to allow removal of large organs or to provide open access to the abdominal cavity 18. Stated another way, the hand seal 120 can be removed at any time to allow conversion from laparoscopic surgery to open surgery.

It is further appreciated that wound retraction in accordance with the present invention allows a surgeon to easily locate the sheath retractor 110 and to provide a base for the hand seal 120. The sheath retractor 110 operates to remove the tissue pressure from the wrist during hand-assisted laparoscopic surgery. The sheath retractor 110 further protects tissue at the wound site, for example, from abrasion, bacteria or other contaminated organs, such as donor kidneys to be removed with minimal risk or damage. The sheath retractor 110 also opens the wound providing greater access to the operative site for instruments, such as the hand of the surgeon. In particular, the sheath protector 110 includes the sheath 116 having elastomeric properties that separate the two rings 112, 114. During surgery, the peritoneal ring 112 is placed interiorly of the abdominal wall 21 and the proximal ring 114 is placed exteriorly of the abdominal wall 21 and is then stretched beyond its natural state. The diameters of the rings 112, 114 are greater than that of the wound site so as to provide sufficient footing and tension between the rings 112, 114. This tension is created by the elastic material that has been stretched and retained at a distance greater than its natural state. It will be appreciated that in other embodiments, the sheath 116 can be formed of a non-elastic sheathing material. In a similar manner, the rings 112, 114 may be provided with a rigid configuration or alternatively may be formed of an elastomeric material.

Referring to FIGS. 3A and 3B, there are shown perspective views of a hand access system 100b where elements of structure similar to those previously described are designated by the same reference numeral followed by the lower case letter "b" in accordance with another embodiment of the invention. The sheath retractor 110b comprises a peritoneal ring 112b, a proximal ring 114b, a sheath 116b extending along an axis 117b connecting the peritoneal ring 112b and the proximal ring 114b, and a one-way mechanism 118b (a cylindrical plug) that is placed to extend above the incision. More specifically, the one-way mechanism 118b is placed between the peritoneal ring 112b and the proximal ring 114b. The hand access system 100b further comprises a "plug" hand seal 120b that is operably attached to the proximal ring 114b of the sheath retractor 110b. The hand seal 120b can be made of a soft gel material including a slit providing an instrument seal in the presence of an instrument or hand and a zero seal in the absence of an instrument or hand. The gel material includes, for example, a thermoplastic base such as Kraton® and an oil. The resulting elastomer has excellent tear strength, elongation greater than 1,000 percent, a very low durometer or hardness, and biocompatibility.

Figure 3C:
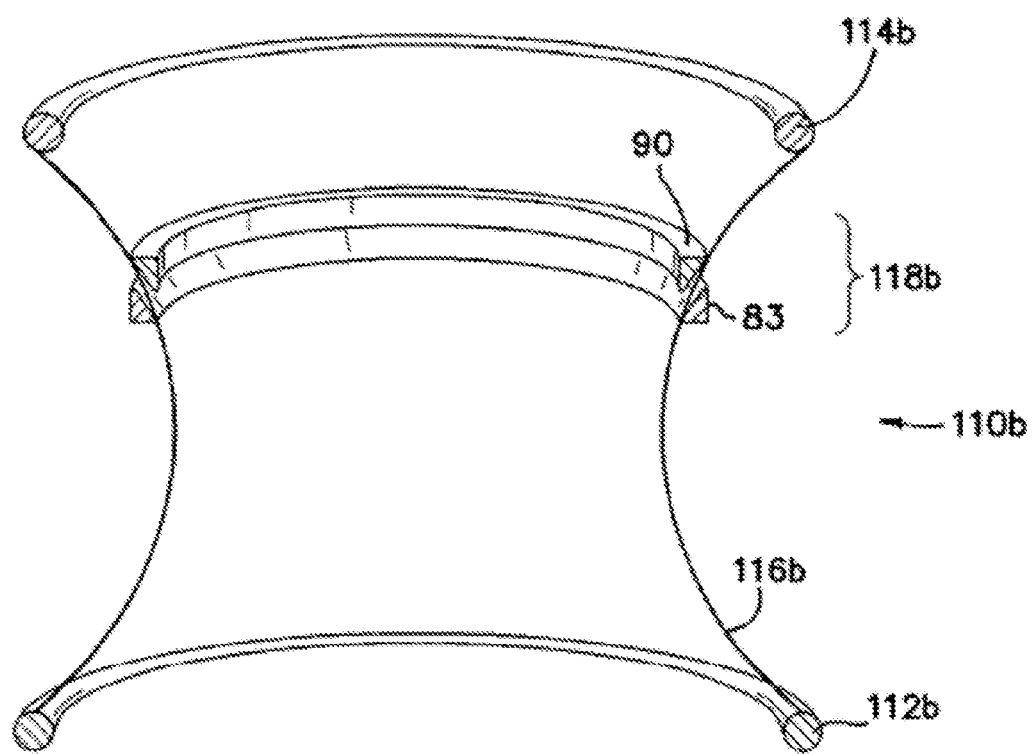
Figure 3D:
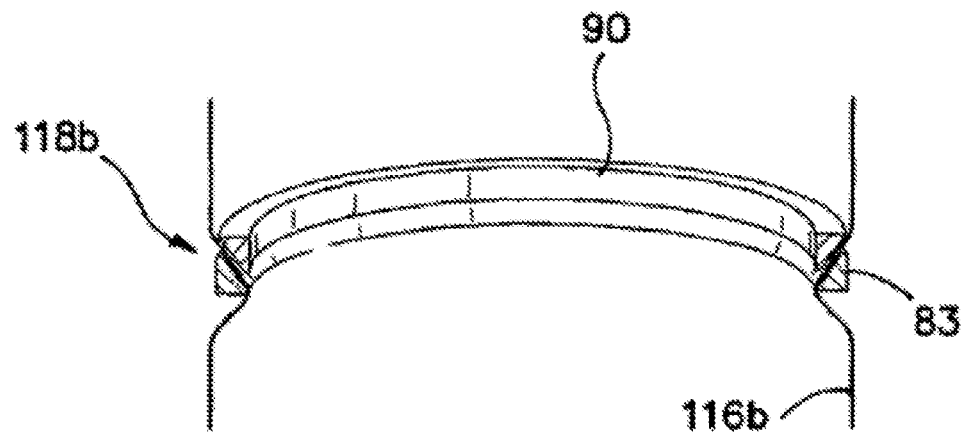
Figure 3E:
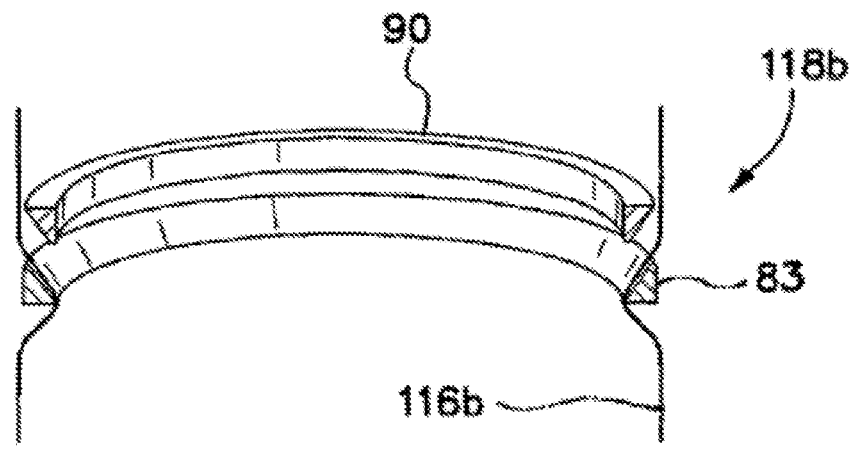

Referring to FIGS. 3C-3E, there are shown axial perspective views of an exemplary embodiment of the one-way mechanism 118b of the invention. Specifically, the one-way mechanism 118b comprises two complimentary interlocking rings 83 and 90. The proximal ring 114b can be disposed outwardly of the sheath 116b and the locking ring 90 can be disposed inwardly of the sheath 116b. These two rings 114b and 90 function to clamp the sheath 116b so that the ring 83 is maintained in a fixed position by the locking ring 90. The interlocking rings 83, 90 of FIG. 3C provide for simple operation of the sheath retractor 110b. These interlocking rings 83, 90 can be pushed down so that they rest on the outer surface of the abdominal wall 21. As the sheath 116b is drawn upwardly to achieve the proper degree of tension, it is easily moved between the interlocking rings 83, 90. However, any tendency of this sheath 116b to move back into the wound site will tighten the interlocking relationship of the rings 83, 90. Thus, the desired degree of tension is maintained on the sheath 116b until it is again pulled to release the locking ring 90 from the ring 83.

The one-way characteristics of the interlocking rings 83, 90 are further illustrated in the progressive views of FIGS. 3D and 3E. With reference to these figures, it can be seen that retraction is maintained by preventing the sheath 116b from pulling back into the wound by means of the one-way operation of the interlocking rings 83, 90. The sheath 116b slides easily through the interlocking rings 83, 90 in the upper direction, but is prevented from sliding through the rings 83, 90 in the downward direction. In order to disengage or separate the interlocking rings 83, 90, one needs only re-tension the sheath 116b by pulling it proximally thereby unlocking the rings 83 and 90. This enables the ring 83 to be removed from the sheath 116b in order to remove the retractor 116b from the wound site.

Figure 4A:
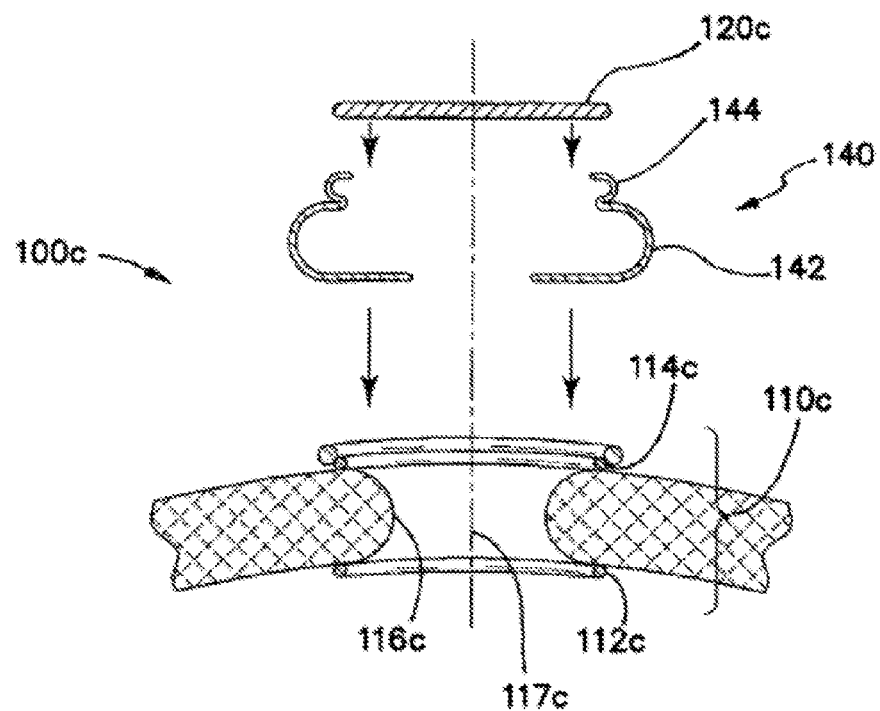
FIGS. 4A and 4B illustrate cross-sectional views of a hand access system in accordance with another embodiment of the invention including an adapter.
Figure 4B:
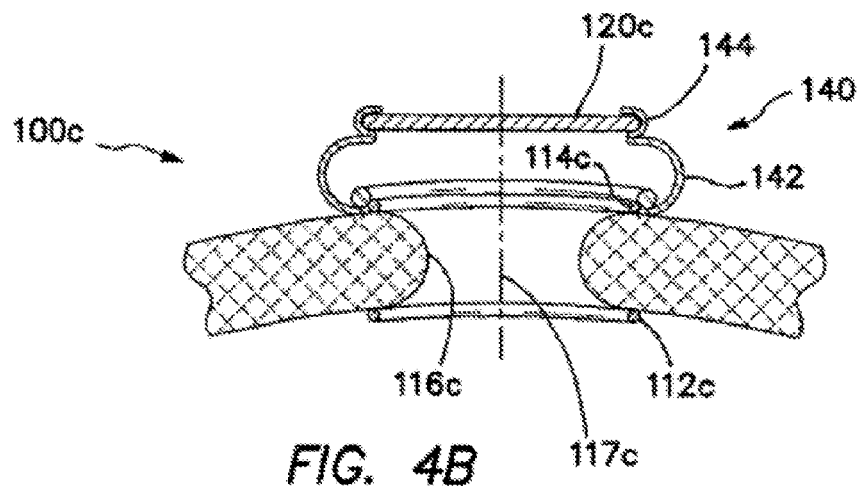

In another aspect of the invention, FIGS. 4A and 4B illustrate axial perspective views of a hand access system 100c comprising a sheath retractor 110c, an adapter 140 and a detachable hand seal 120c. The sheath retractor 110c includes a peritoneal ring 112c, a proximal ring 114c, and a sheath 116c extending along an axis 117c connecting the peritoneal ring 112c and the proximal ring 114c. The adapter 140 comprises a first or lower ring 142 for attaching to the proximal ring 114c of the sheath retractor 110c, and a second or upper ring 144 for attaching to the detachable hand seal 120c. FIG. 4B illustrates the hand access system 100c with the sheath retractor 110c, the adapter 140 and the hand seal 120c installed. More specifically, the adapter 140 is first attached to the proximal ring 114c of the sheath retractor 110c. In turn, the hand seal 120c may be attached and detached from the upper ring 144 of the adapter 140 as needed.

It is appreciated that the proximal ring 114c may further include a movable ring, which together with the proximal ring 114c, may be used to press down on the adapter 140 against the abdomen, for example, to secure it and form an airtight connection. It is further appreciated that the upper ring 144 may have a diameter that is greater than, equal to or less than the diameter of the lower ring 142. In another aspect of the invention, the adapter 140 may further comprise grooves to snap in a self-closing iris seal to gain pneumoperitoneum.

Figure 5A:
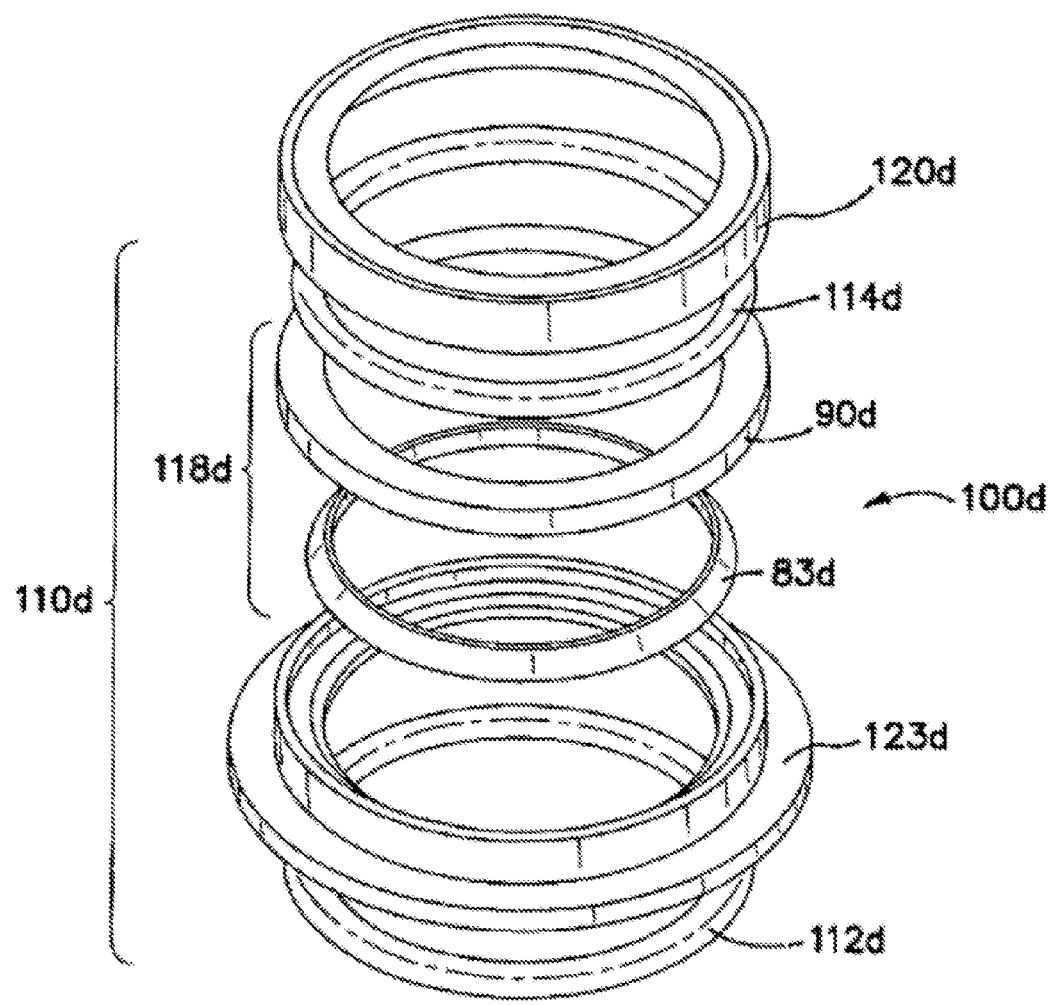
FIGS. 5A-5C illustrate an axial perspective view and cross-sectional views of a hand access system in accordance with another embodiment of the invention including a conformable gasket.
Figure 5B:
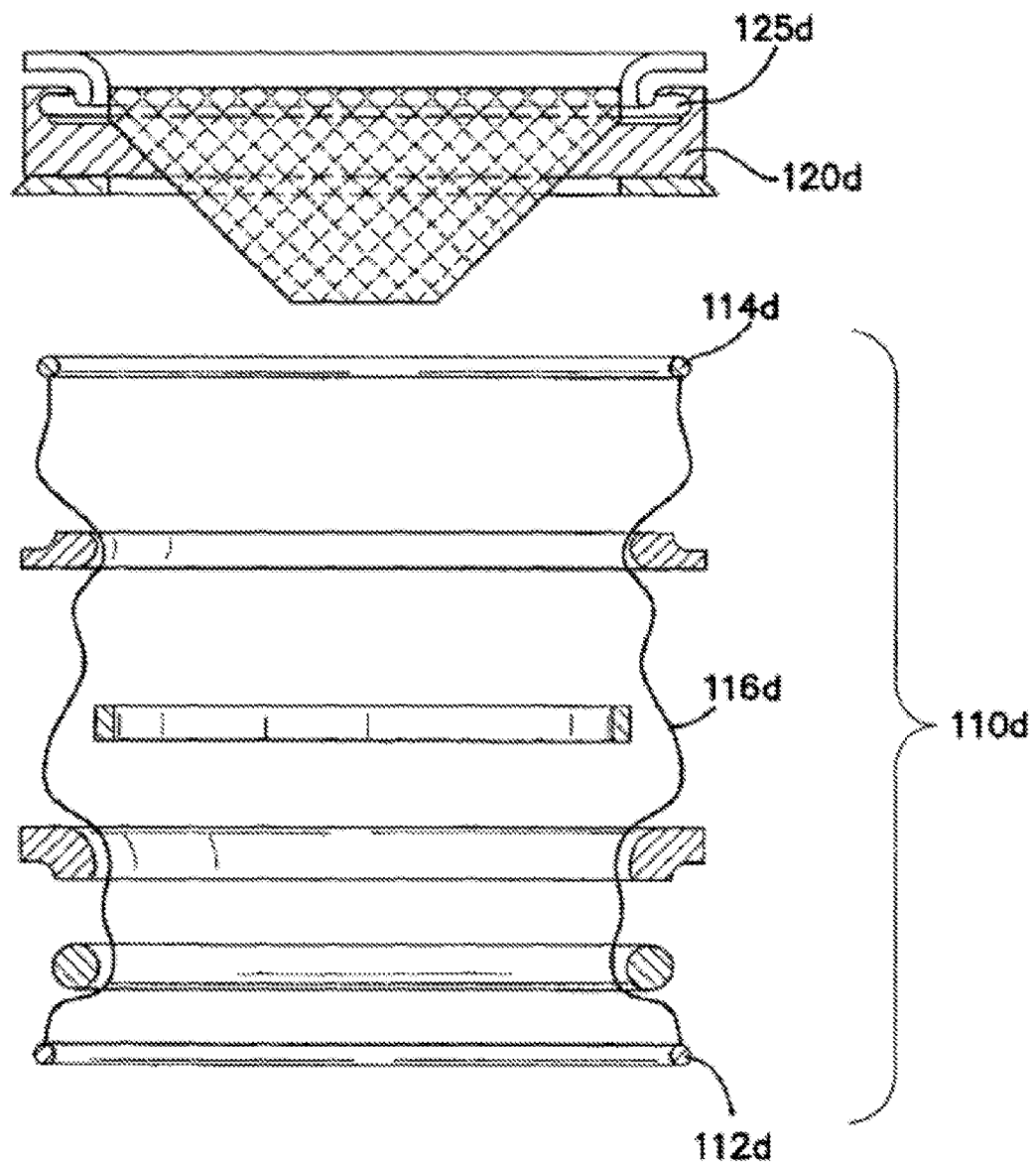
Figure 5C:
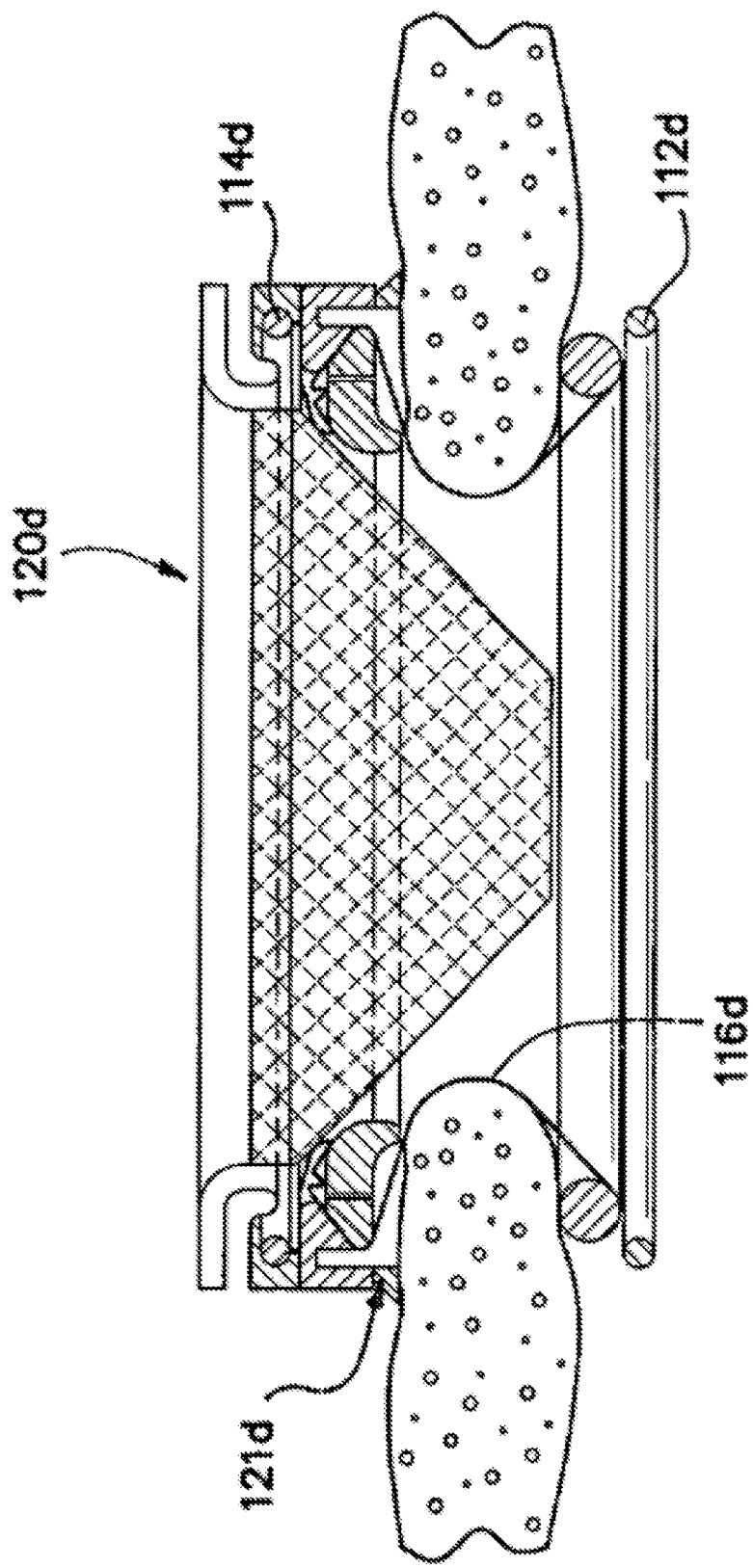

FIGS. 5A-5C illustrate perspective and cross-sectional views of a hand access system 100d in accordance with yet another embodiment of the invention where elements of structure similar to those previously described are designated by the same reference numeral followed by the lower case letter "d". The hand access system 100d comprises a sheath retractor 110d and a hand seal 120d operably attached to the sheath retractor 110d. The sheath retractor 110d includes a peritoneal ring 112d, a proximal ring 114d, a sheath (not shown) connecting the peritoneal ring 112d and the proximal ring 114d, and a one-way mechanism 118d comprising a plurality of interlocking rings 83d, 90d. The hand seal 120d operably attaches to the proximal ring 114d of the sheath retractor 110d. The hand seal 120d may be formed of a soft gel material and includes a small slit to allow passage of a hand or a surgical instrument during surgery. Referring to FIG. 5B, there is shown a cross-sectional view of the hand seal 120d having a cavity 125d inside the gel to receive the proximal ring 114d of the sheath retractor 110d. Referring to FIG. 5C, the hand seal 120d may further comprise a latch 121d on an inner diameter for latching the one-way mechanism 118d. The access sheath material may be placed inside or outside of the hand seal 120d after attachment of the hand seal 120d and the seal retractor 110d.

In another aspect, the one-way mechanism 118d may include hooks to latch the hand seal 120d as the seal 120d is pressed down on the open end of the sheath. As explained above, the hand seal 120d includes a small slit in the gel that will not allow air to pass with the absence of an instrument or hand, but the slit will stretch and the gel will compress to allow objects to pass through with little loss of pneumoperitoneum. Compression of the gel onto the proximal ring 114d of the sheath retractor 110d creates an airtight connection. The sheath retractor 110d, as illustrated in FIG. 5A, may further include a conformable gasket 123d to facilitate sealing of the peritoneum. The conformable gasket 123d on the peritoneum ensures an airtight seal inside the incision as opposed to outside the incision. The gasket 123d can be attached to the peritoneal ring 112d or the sheath 116d, or it can float unattached to the sheath. The floating gasket 123d is less likely to crease or bunch (a path for air leaks) as the abdominal wall 21, sheath 116d and peritoneal ring 112d distort as the sheath 116d is pulled up into the incision. Without the need for sealing externally on the skin surface, the conformable gasket 123d is not susceptible to air leaks from irregularities on the skin, such as scars or folds. Furthermore, the conformable gasket 123d protects the abdominal wall 21 from potential traumatic pressure or abrasion by the peritoneal ring 112d.

In all of the above embodiments of the invention, the ability to attach and detach the hand seal from the sheath retractor allows larger objects to pass unfettered through the incision.

In addition, the invention is easy to use, it provides increased comfort for the surgeon, and is less traumatic to tissue being passed through the incision. For example, the latching or interlocking feature of the hand seal and the adapter with the sheath retractor makes it fast and simple to use compared to other methods that may involve inflatable cuffs or adhesives. Adhesives often require time to cure and inflation with pumps also creates delay.

Figure 6:
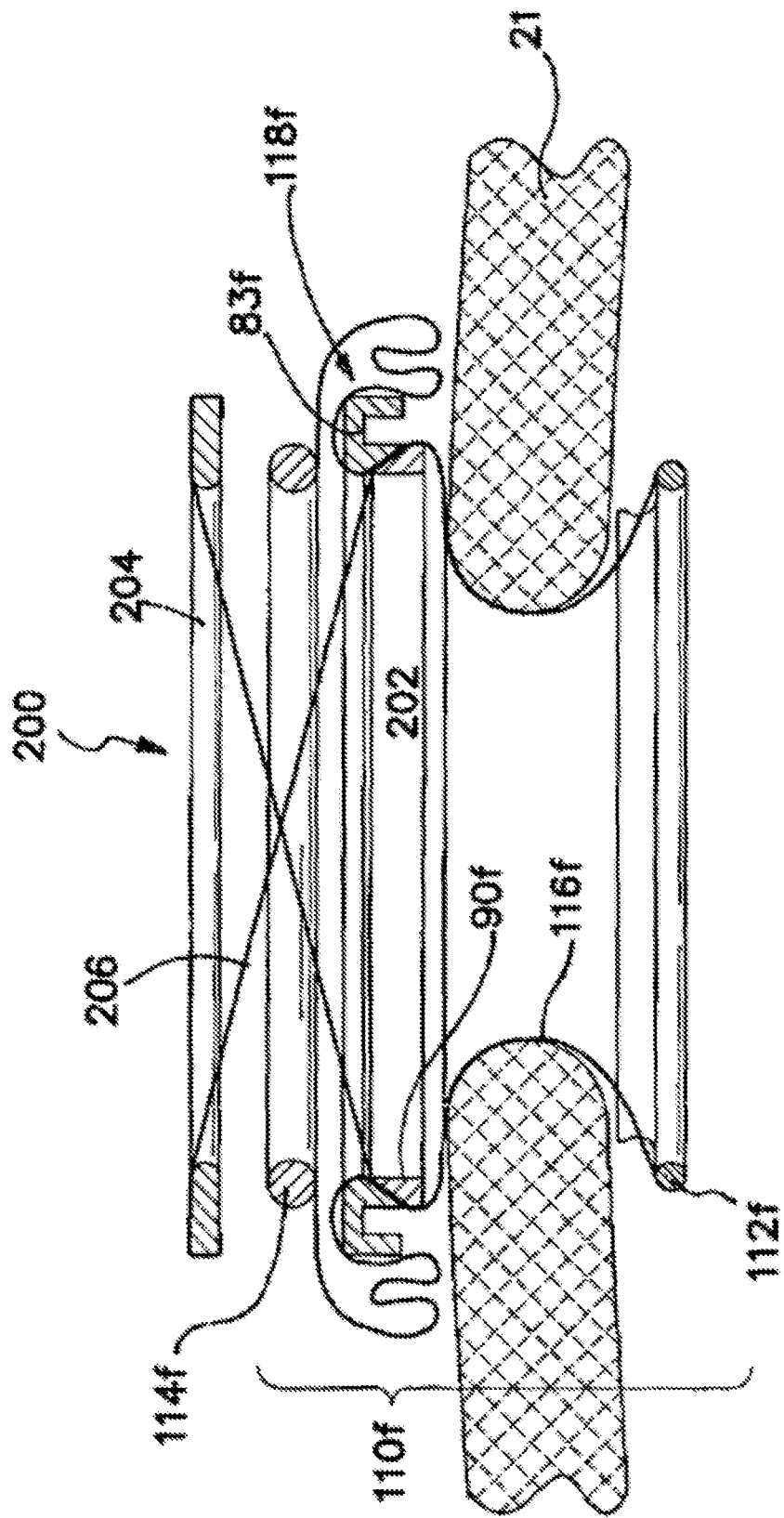
FIG. 6 illustrates a cross-sectional view of a hand access system in accordance with another embodiment of the invention including an iris seal.
Figure 7A:
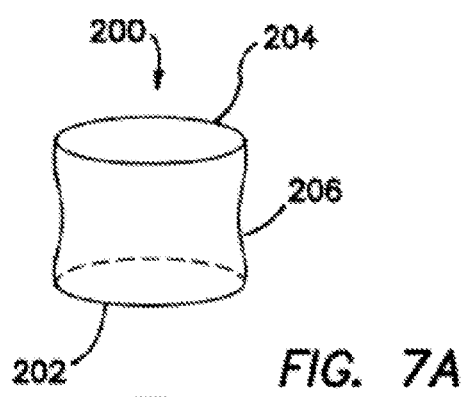
FIGS. 7A-7E illustrate the rotation of the iris seal rings of the invention to create an airtight constriction in the middle of the sheath.
Figure 7B:
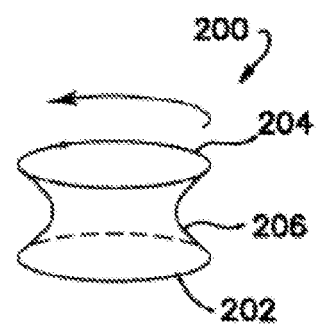
Figure 7C:
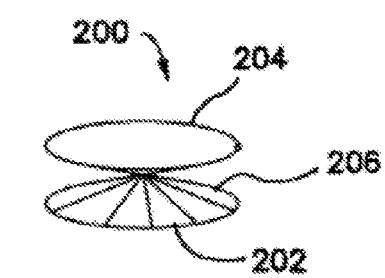
Figure 7D:
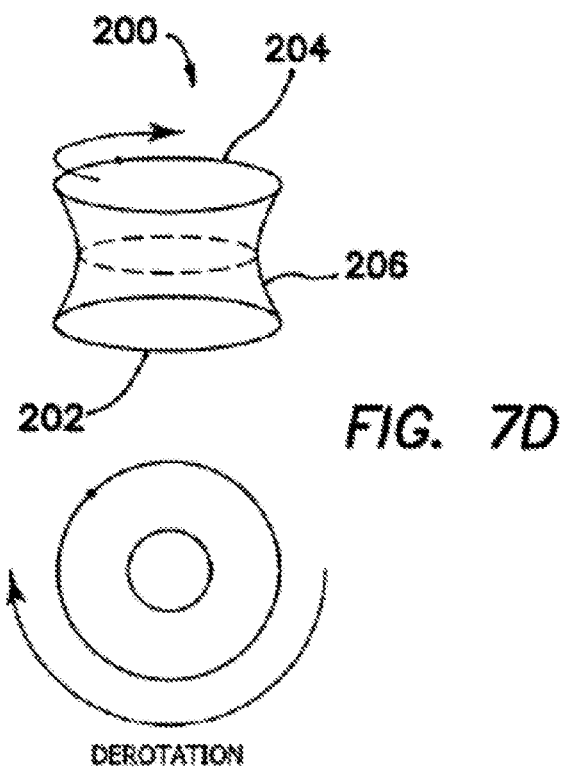
Figure 7E:
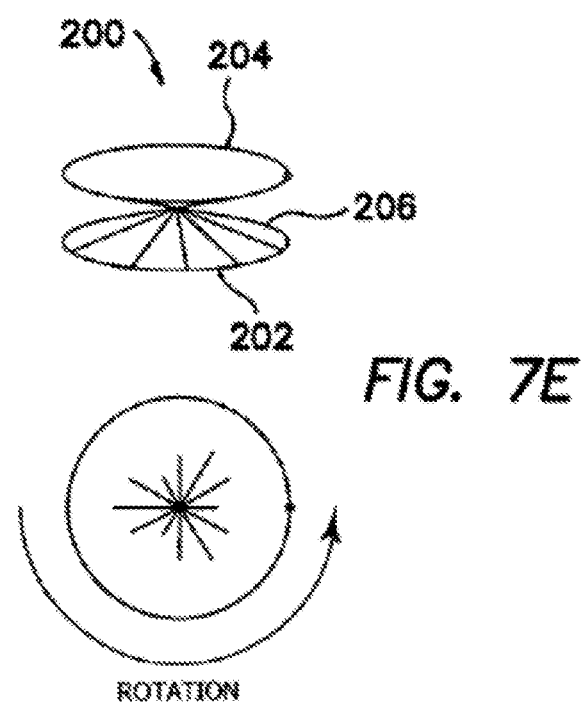

In another aspect of the invention, the hand access system may comprise a sheath retractor and an iris seal directly connected to the sheath retractor to form a continuous, seamless sheath. Referring to FIG. 6, there is shown a hand access system in accordance with another embodiment of the invention including an iris seal 200. The iris seal 200 comprises a first ring 202, a second ring 204 coaxially attachable to the first ring 202, and a cylindrical elastic member 206 connected to the first and second rings 202, 204 and having an opening. The first and second rings 202, 204 operate to rotate relative to one another in either direction to open or close the opening of the cylindrical elastic member 206. In particular, the seal 200 operates like the iris aperture of a camera, except that the iris seal 200 is made of a thin film sheath or elastic member 206. A ring 202, 204 is attached to each end of the sheath or elastic sheath 206. Referring to FIGS. 7A-7C, the rings 202, 204 are rotated in opposite directions to create an airtight constriction in the middle of the sheath or elastic member 206. The constriction is maintained as long as the rotation is not undone (termed de-rotation). The sheath or elastic member 206 can be made of an elastic material, which allows objects small in diameter relative to the rings 202, 204 to pass easily through the constriction without the need for de-rotation. However, objects with large diameters may require de-rotation to loosen or enlarge the constriction in the sheath as illustrated in FIG. 7D. Once an object is withdrawn, the rings 202, 204 must rotate back to create the airtight constriction as illustrated in FIG. 7E. In another aspect, the rings 202, 204 may include a plurality of tracks 207 such that they may be relatively rotated to open or close the opening at predetermined angles as further discussed below and illustrated in FIG. 10. More specifically, the sectional area of the opening changes in response to the predetermined angle rotation of the rings.

Referring back to FIG. 6, the iris seal 200 may be attached to a sheath retractor 110f having a peritoneal ring 112f, a proximal ring 114f, a sheath 116f connecting the peritoneal ring 112f and the proximal ring 114f, and a one-way mechanism 118f (comprising a plurality of interlocking rings 83f, 90f). A feature of the iris seal 200 is its constriction can be dilated as wide as the retracted incision and, as such, it may not be necessary for it to be detached from the sheath retractor 110f. In this case, the iris seal 200 can be made a permanent part of one of the interlocking rings of the one-way mechanism 118f. Thus, the self-closing iris seal 200 and sheath retractor 110f combination allows pneumoperitoneum to be regained more quickly without having to detach and reattach a seal as with previous methods. In another aspect, an iris seal can be easily removed when constructed as part of a two-ring design in the form of a wedge clamp similar to that shown in FIGS. 3C-3E. Pulling up on a sheath pushes or un-wedges the seal out of the sheath retractor.

Figure 8A:
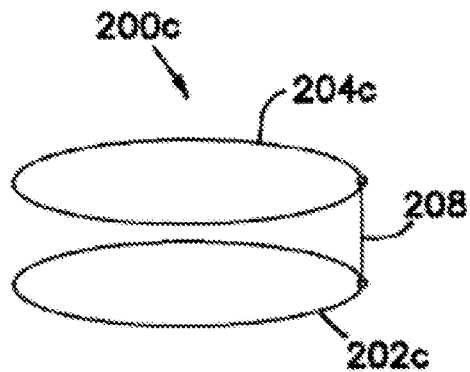
FIGS. 8A-8C illustrate side views of another embodiment of the iris seal including a spring connecting the two rings.
Figure 8B:
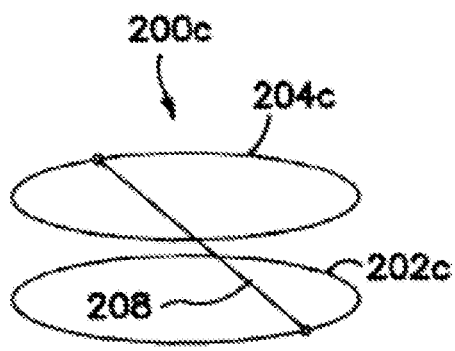
Figure 8C:
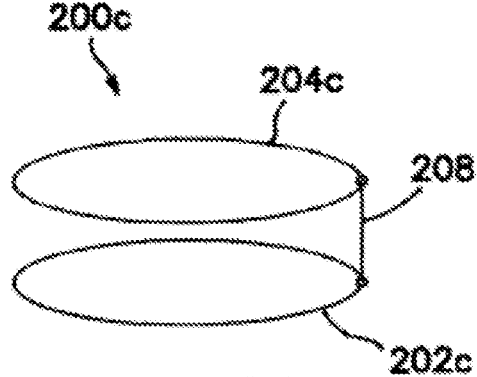
Figure 9:
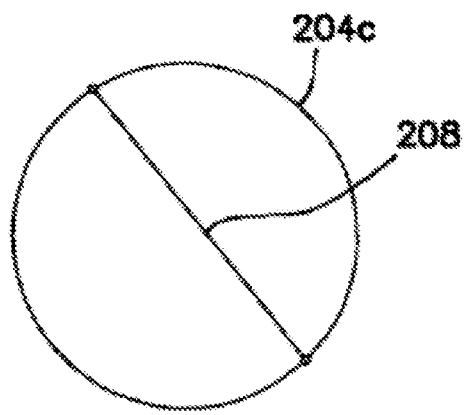
FIG. 9 illustrates a top view of FIG. 8B.

It is appreciated that other hand seals can be used and interchanged as contemplated by the concept of the invention. For example, the iris seal of the invention may further include a spring 208 connecting the first and second rings 202, 204 to further facilitate the opening and closing of the opening of the cylindrical elastic member 206. More particularly, one or more springs 208 may be used to connect the first and second rings 202, 204 to provide a complete opening, a partial constriction or an airtight constriction of the iris seal. Referring to FIGS. 8A-8C, there are shown perspective views of the iris seal 200c of the invention further comprising the spring 208 connecting the first and second rings 202c, 204c. FIG. 9 is a top view of the iris seal 200c of FIG. 8B.

Figure 10:
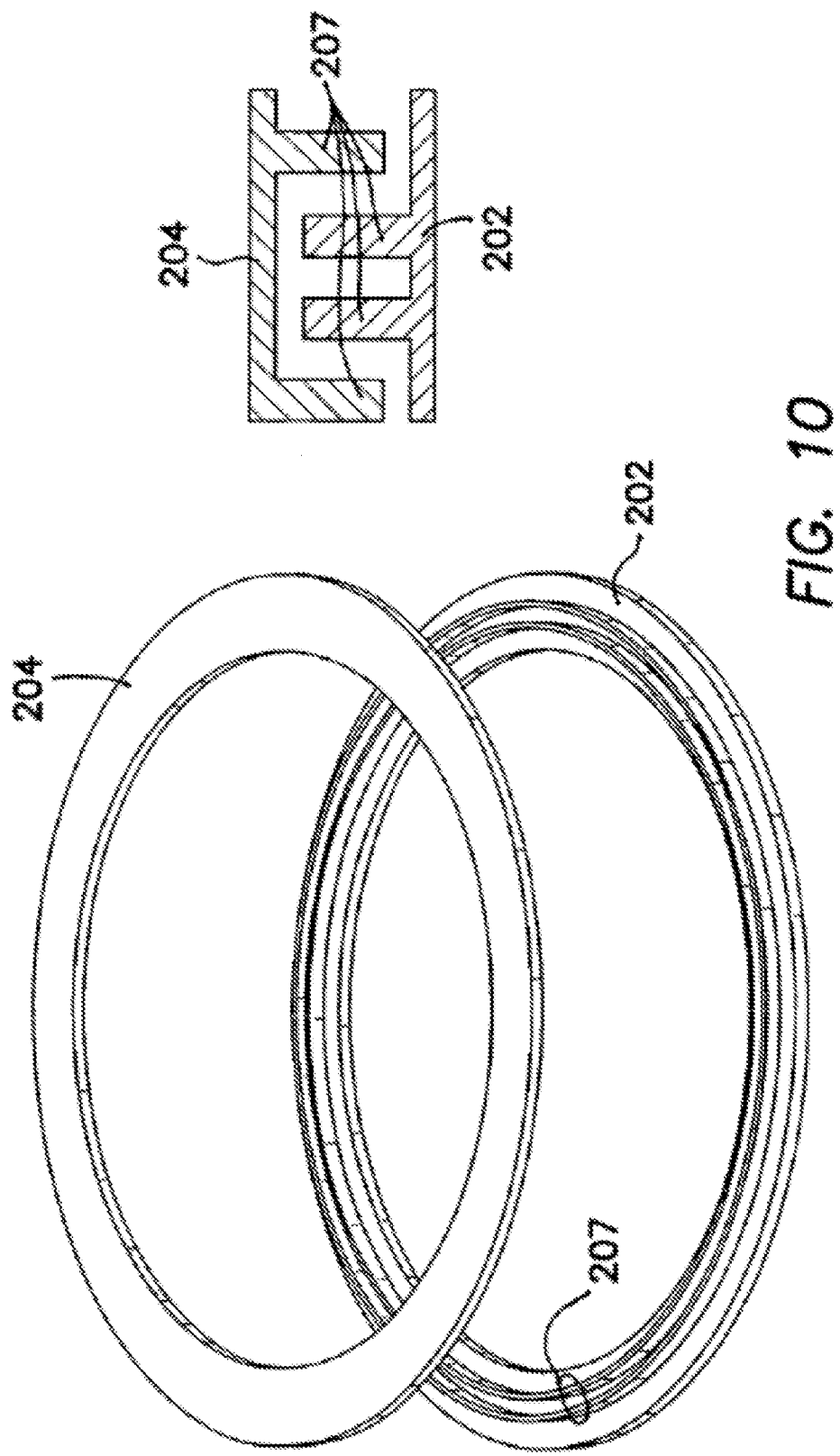
FIGS. 10 and 11A-B illustrate perspective and top views of rings of an iris seal having interlocking tracks in accordance with another embodiment of the invention.
Figure 11A:
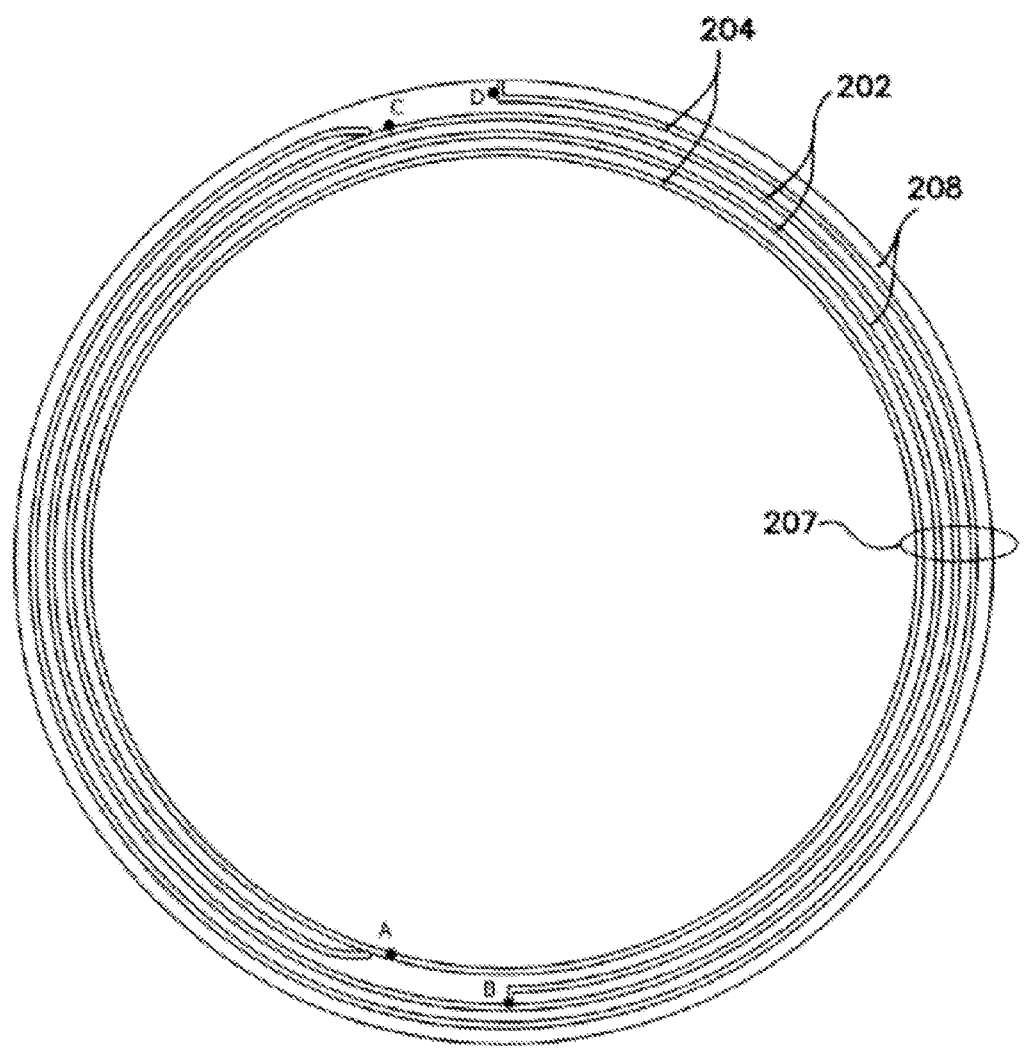
Figure 11B:
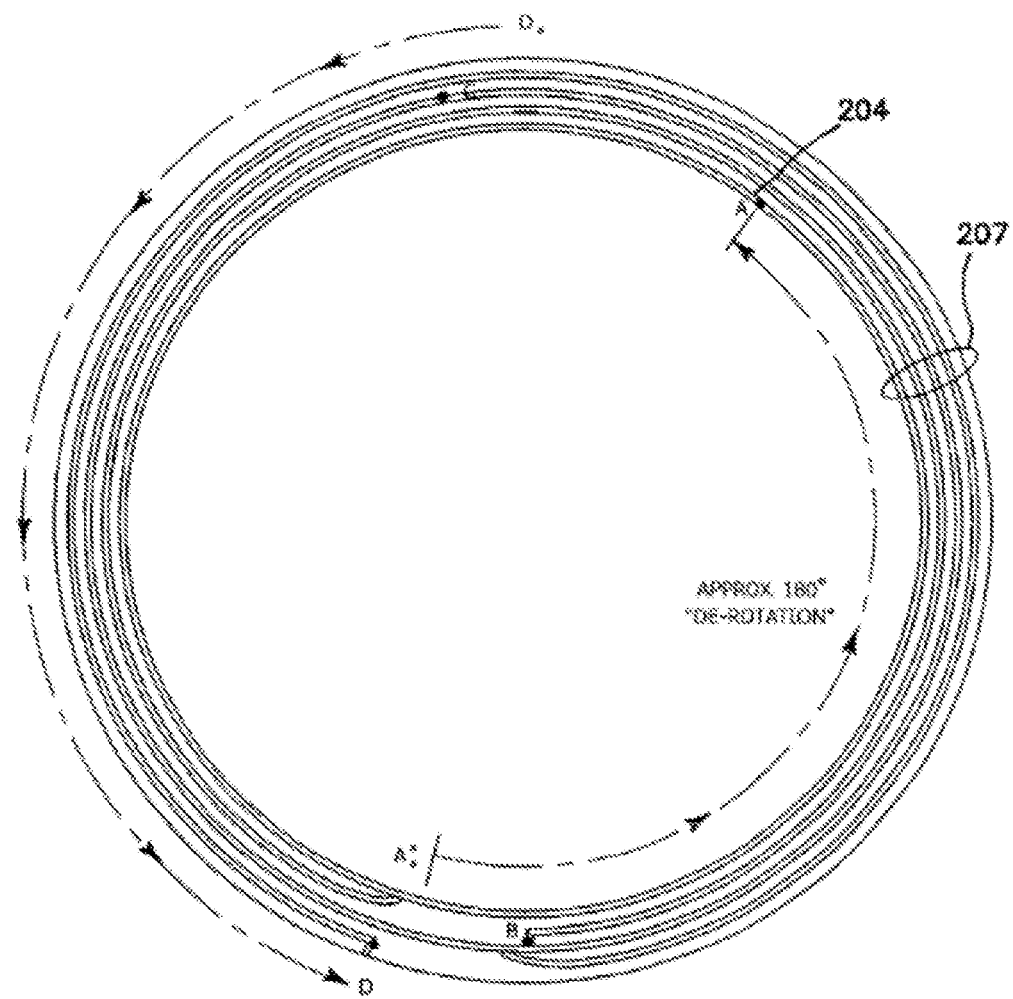

As illustrated in FIGS. 8 and 9, as the rings 202c, 204c are rotated relative to one another, the spring 208 expands and contracts causing opening and constriction of the seal. More specifically, the spring 208 can be used to pull and rotate the rings 202c, 204c automatically after de-rotation, for example. The ends of the spring 208 are connected to the rings 202c, 204c in a manner such that de-rotation causes the spring 208 to stretch as illustrated in FIGS. 8A and 8B. Afterwards, the spring 208 contracts and causes the sheath constriction to tighten automatically as large objects are withdrawn (FIG. 8C). The amount the spring 208 stretches and contracts is determined by the length of the spring 208—typically larger objects require longer springs. Longer springs, however, may crossover the area within the rings 202c, 204c and interfere with the passage of objects as illustrated in FIG. 9. To limit interference and to accommodate large objects, longer springs can be housed partially within a series of interlocking tracks 207 of hollow frame rings 202d, 204d as illustrated in FIGS. 10 and 11A-B. In particular, the interlocking tracks 207 on the rings can encase longer springs so they do not cross into the passage area. The interlocking tracks 207 also operate to open and close the seal at predetermined angles. FIG. 11A illustrates an axial cross-sectional view of the seal with the springs contracted and the iris closed, and FIG. 11B illustrates an axial cross-sectional view of the seal with the springs expanded and the iris opened.

An advantage of rotational adjustment, versus fixed rings, is that a wider range of object sizes can easily pass through the iris seal. A self-closing mechanism of the invention has the advantage of hands-free adjustment. In comparison to other self-closing methods that involve gears and springs that are connected to stationary components external to the iris seal, the spring(s) of the present invention are connected to and contained within the rings, which are integral to the iris seal. With the self-closing mechanism built in, the iris seal is portable and can be more easily adapted to a wide range of access ports, wound retractors and the like.

Figure 12:
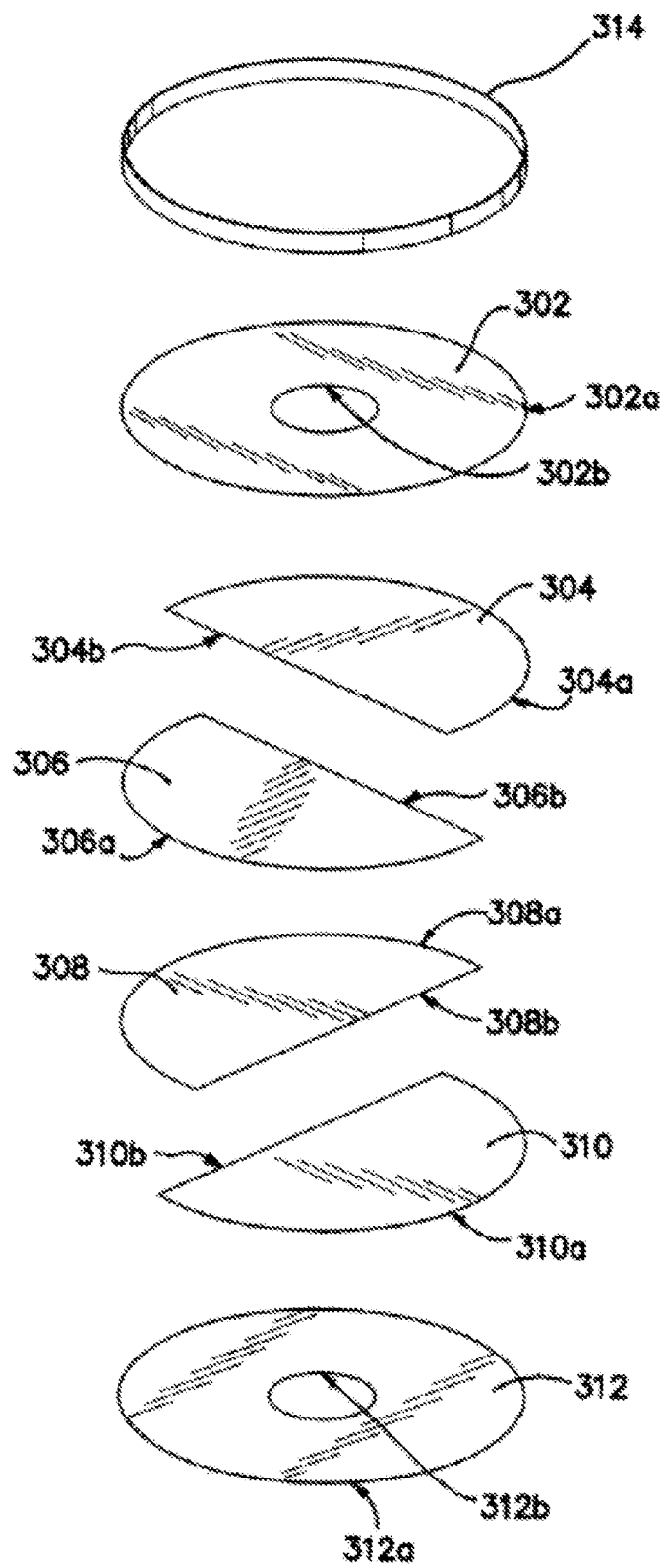
FIG. 12 illustrates a perspective view of a hand-assisted laparoscopic seal formed by overlapping sheets of elastomeric material in accordance with another embodiment of the invention.

In another aspect of the invention, a hand-assisted laparoscopy seal 300 is formed by overlapping several sheets 302, 304, 306, 308, 310, 312 of elastomeric material as illustrated, for example, in FIG. 12. Each of these sheets 302, 304, 306, 308, 310, 312 is fixed along a portion of its perimeter to the circumference of a semi-rigid or rigid ring (not shown). As a result, each of the sheets 302-312 has at least a portion 302a, 304a, 306a, 308a, 310a, 312a of its perimeter fixed to the ring and a portion 302b, 304b, 306b, 308b, 310b, 312b not fixed to the ring. These non-fixed portions 302b-312b provide open edges within the area of the ring. The sheets 302-312 are laid on top of one another and are rotated so that open edges extend along different planes. These open edges slightly overlap, such as approximately one-quarter inch, at the center of the ring to prevent leakage of the insufflation gas. During operation, an instrument or hand of the surgeon is introduced through the center of the ring forcing the open edges to part, but also causing the open edges to form a sealing structure around the forearm or wrist.

Figure 13:
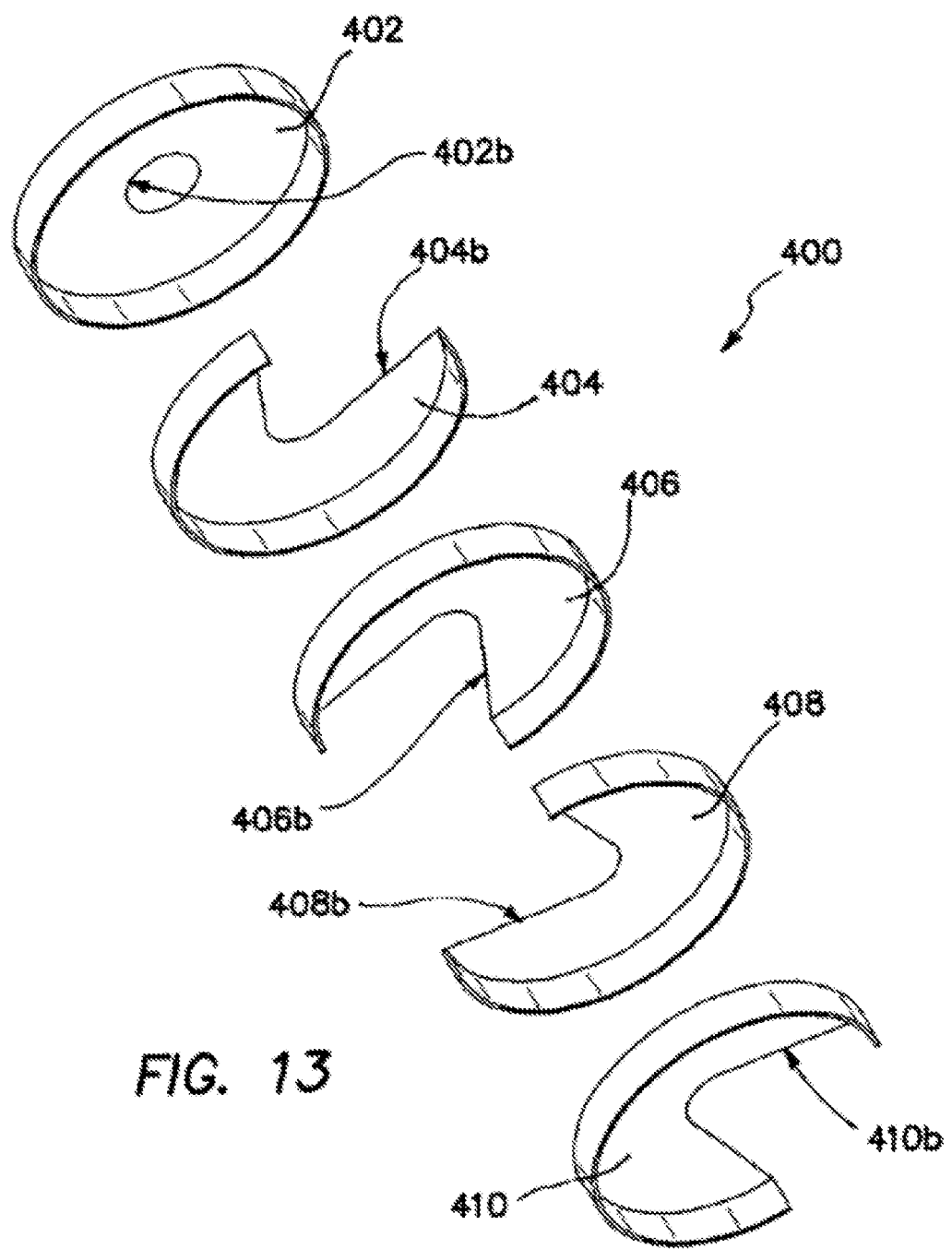
FIG. 13 illustrates a perspective view of a hand-assisted laparoscopic seal formed by differently shaped overlapping sheets of elastomeric material in accordance with another embodiment of the invention.

It is appreciated that in the above aspect, the overlapping sheets 302, 312 may comprise two septum sheets having their full perimeters fixed to the ring and a hole formed at the center of the septum sheets. Referring to FIG. 13, there is shown another aspect of the invention where the open edges 404b, 406b, 408b, 410b have different shapes, which when laid on top of one another, tend to form overlapping sections of a circle. It is appreciated that the concept of the invention contemplates any number of overlapping sheets of any material and of any shape. In one simple embodiment, for example, the invention contemplates two semi-circular sheets having slightly straight overlapping edges.

Figure 14:
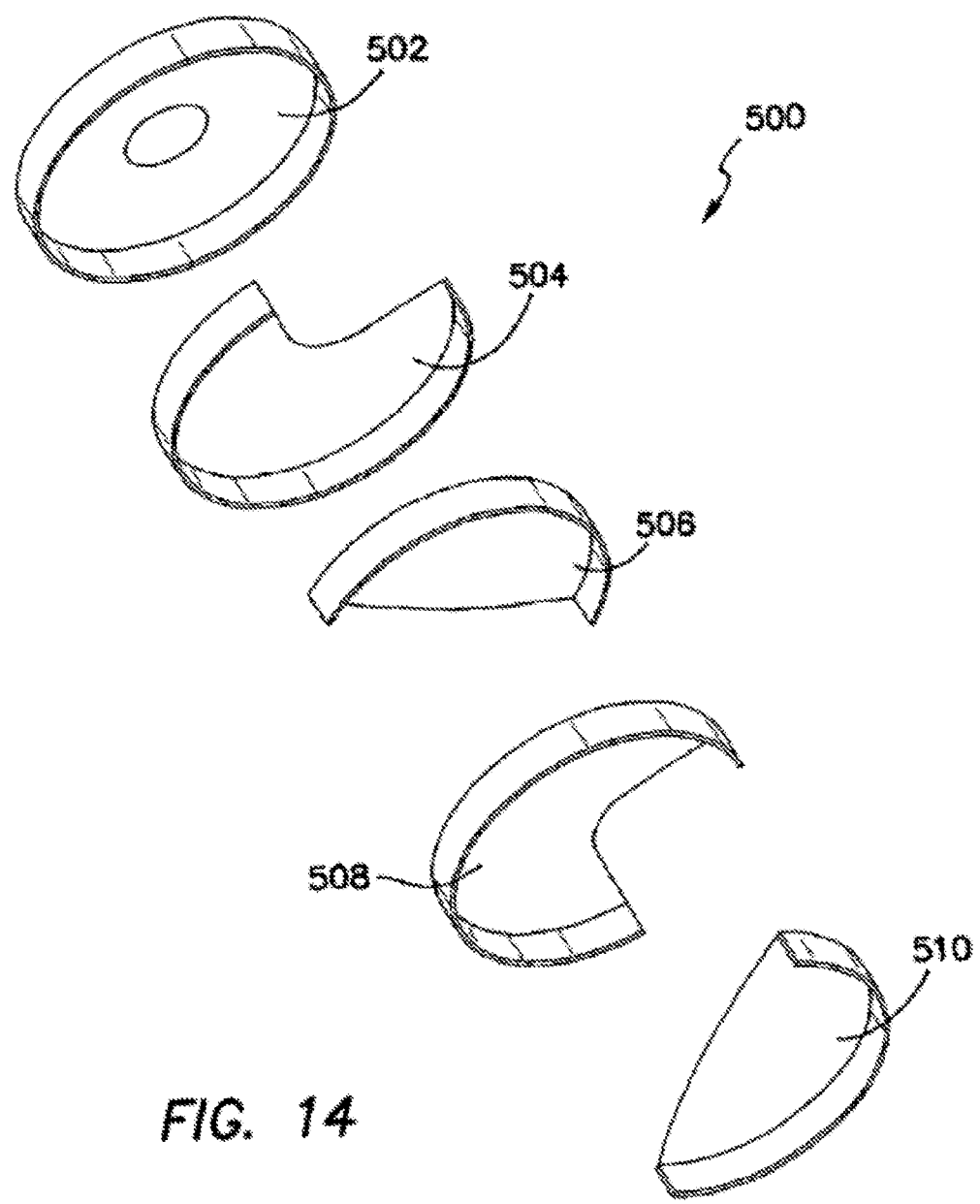
FIGS. 14 and 15 illustrate perspective views of a hand-assisted laparoscopic seal formed by overlapping sheets of elastomeric material having concave and convex configurations.
Figure 15:
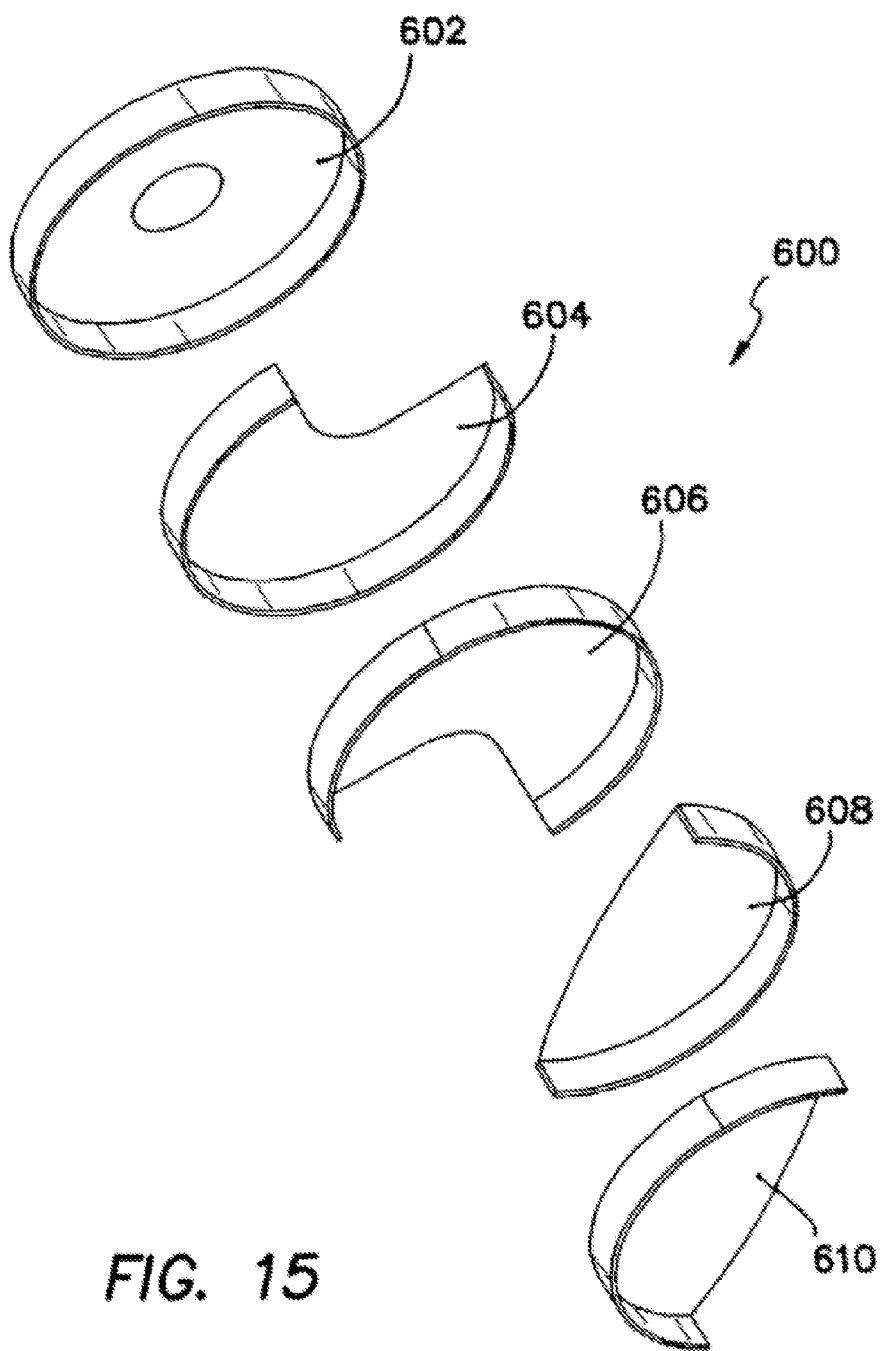
Figure 16:
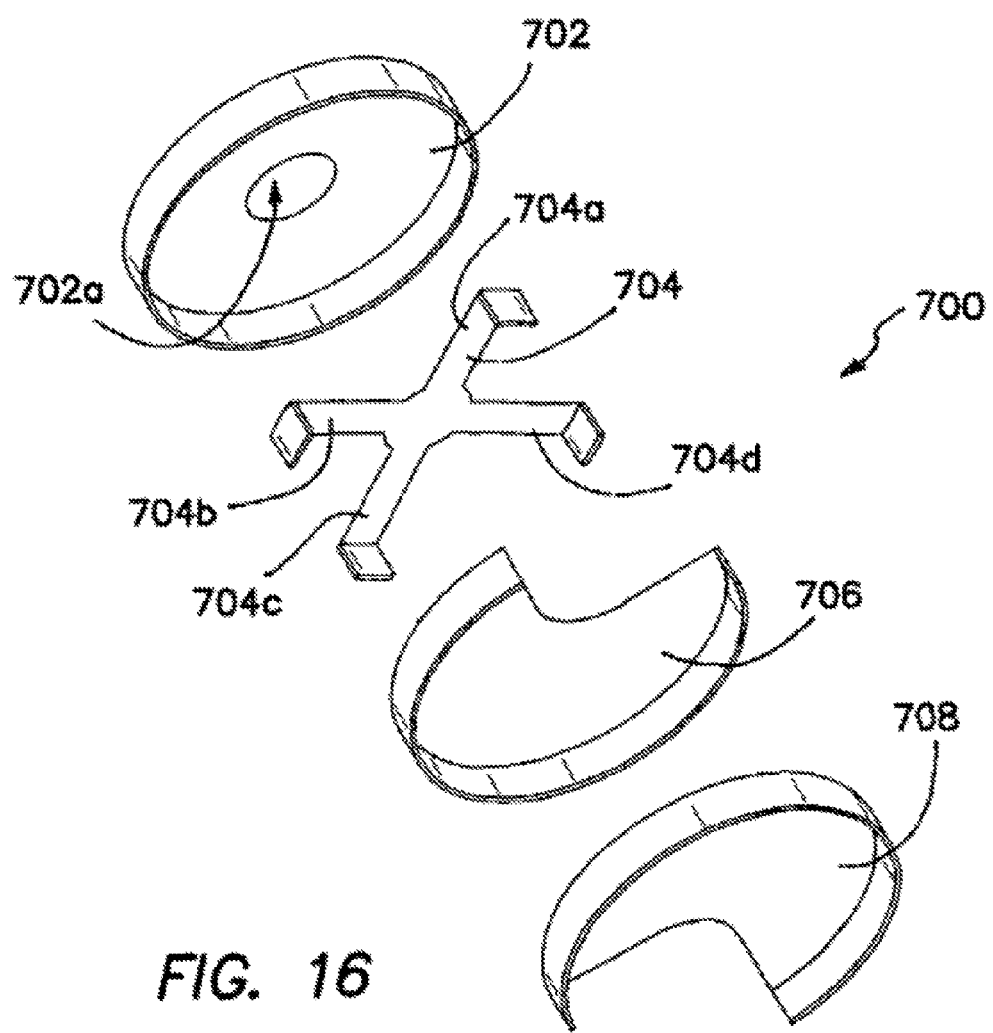
FIG. 16 illustrates a perspective view of a hand-assisted laparoscopic seal formed by overlapping sheets of elastomeric material including a central patch supported by spokes in accordance with another embodiment of the invention.
Figure 17:
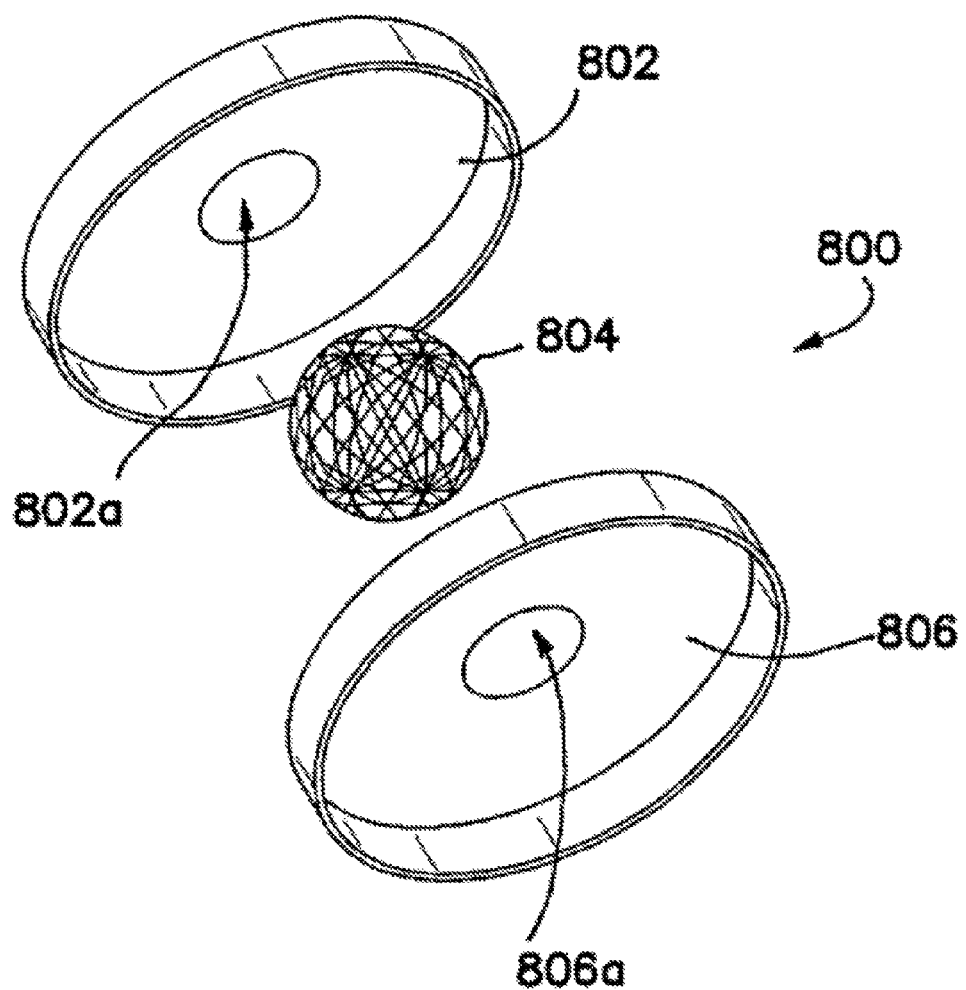
FIG. 17 illustrates a perspective view of a hand-assisted laparoscopic seal formed by two septum layers sandwiching a ball in accordance with another embodiment of the invention.

In another aspect, FIGS. 14 and 15 show how the open edges can be provided with concave or convex configurations. The sheets or layers having convex open edges 506, 510, 608, 610 tend to flex more while the sheets or layers having concave edges 504, 508, 604, 606 tend to give more support. The septum sheets or layers 502, 602 provide the most support. Other shapes can be used for the layers as illustrated in the embodiment of FIG. 16 where one of the layers includes a central patch 704 supported by spokes 704a, 704b, 704c, 704d which extend to the ring. The central patch 704 is large enough to cover the hole 702a in the septum layer 702. In the embodiment of FIG. 17, two septum layers 802, 806 sandwich a ball 804 which is movable within the confines of the ring. The ball 804 has a diameter greater than the holes 802a, 806a in the septum layers 802, 806, respectively.

It will be understood that many other modifications can be made to the various disclosed embodiments without departing from the spirit and scope of the invention. For these reasons, the above description should not be construed as limiting the invention, but should be interpreted as merely exemplary of the disclosed embodiments.

The invention claimed is:

1. A surgical access device comprising:
   a valve structure comprising:
      a plurality of septum layers; and
      a ring having an inner diameter for affixing the plurality of septum layers along their perimeter;
   wherein the plurality of septum layers includes a first septum layer having a hole at a center of the first septum layer;
   wherein the plurality of septum layers comprises a second septum layer comprising a central patch supported by a plurality of spokes extending from the central patch, the central patch being large enough to cover the hole of the first septum layer;
   wherein the valve structure in a first state forming a zero seal in the absence of the instrument or the arm of the surgeon extending through the valve structure, the valve structure in a second state forming an instrument seal in the presence of the instrument or the arm of the surgeon extending through the valve structure and into a patient.

2. The surgical access device of claim 1 wherein the plurality of septum layers includes a third septum layer having an open edge and a fourth septum layer having an open edge.

3. The surgical access device of claim 2 wherein the open edges of the third septum layer and the fourth septum layer slightly overlap at a center of the ring.

4. The surgical access device of claim 2 wherein the open edges of the third septum layer and the fourth septum layer have a concave configuration.

5. The surgical access device of claim 4 wherein the ring is rigid.

6. The surgical access device of claim 4 wherein the second septum layer and the third septum layer are disposed between the first septum layer and the fourth septum layer.

7. The surgical access device of claim 4 wherein the plurality of septum layers are made of elastomeric material.

* * * * *